(12) United States Patent
McCann et al.

(10) Patent No.: US 10,753,778 B2
(45) Date of Patent: Aug. 25, 2020

(54) METHOD AND APPARATUS FOR MONITORING THE FLOW OF MIXTURES OF FLUIDS IN A PIPE

(71) Applicant: iPhase Limited, Oxford (GB)

(72) Inventors: Dominic Patrick McCann, Oxford (GB); Kevin John Forbes, Oxford (GB); Andrew Hunt, Oxford (GB)

(73) Assignee: iPhase Limited, Oxford (GB)

( * ) Notice: Subject to any disclaimer, the term of this patent is extended or adjusted under 35 U.S.C. 154(b) by 0 days.

(21) Appl. No.: 16/450,971

(22) Filed: Jun. 24, 2019

(65) Prior Publication Data

US 2019/0316943 A1 Oct. 17, 2019

Related U.S. Application Data

(63) Continuation of application No. 14/888,019, filed as application No. PCT/EP2014/058907 on Apr. 30, 2014, now Pat. No. 10,378,941.

(30) Foreign Application Priority Data

Apr. 30, 2013 (GB) .................................... 1307785.4

(51) Int. Cl.
*G01F 1/74* (2006.01)
*G01N 33/28* (2006.01)
(Continued)

(52) U.S. Cl.
CPC ................ *G01F 1/74* (2013.01); *E21B 47/10* (2013.01); *G01F 1/58* (2013.01); *G01N 33/2823* (2013.01);
(Continued)

(58) Field of Classification Search
CPC ......... G01F 1/74; G01F 1/58; G01N 33/2823; G01N 27/02; G01P 5/18; E21B 47/10; G01V 3/104
See application file for complete search history.

(56) References Cited

U.S. PATENT DOCUMENTS 4,228,353 A 10/1980 Johnson
4,868,856 A 9/1989 Frith et al.
(Continued)

FOREIGN PATENT DOCUMENTS

EP 0 420 109 A1 4/1991
EP 2 343 538 A2 7/2011
(Continued)

OTHER PUBLICATIONS

Examination Report under Section 18(3) from GB1319517.7, dated Nov. 6, 2014.
(Continued)

*Primary Examiner* — Herbert K Roberts
*Assistant Examiner* — John M Royston
(74) *Attorney, Agent, or Firm* — Hamilton, Brook, Smith & Reynolds, P.C.

(57) ABSTRACT

A monitoring apparatus for monitoring a multiphase flow in a pipe, the apparatus comprising: a first monitoring module coupled to the pipe and adapted to provide first output data representing a respective concentration of one phase of a plurality of phases, or a mixture of at least two of the phases, in the multiphase flow by processing at least one first variable representing electrical permittivity of one phase or a mixture of at least two of the phases of the multiphase flow; a second monitoring module coupled to the pipe and adapted to provide second output data representing a respective concentration of one phase, or a mixture of at least two of the phases, of the plurality of phases in the multiphase
(Continued)

flow by processing at least one second variable representing electrical conductivity of one phase or a mixture of at least two of the phases of the multiphase flow; and a third monitoring module coupled to the pipe and adapted to provide third output data representing a respective velocity of at least one phase of the plurality of phases in the multiphase flow by processing at least one third variable representing velocity of at least one of the phases. There is a further provided a monitoring method for monitoring a multiphase flow in a pipe. There is a further provided an oil well system including a plurality of oil wells, and one or more monitoring apparatus for monitoring a multiphase flow in a pipe. There is a further provided a method of operating an oil well system using a multiphase fluid flow model which is calibrated or modified based on measured parameters of the multiphase flow.

5 Claims, 23 Drawing Sheets

(51) Int. Cl.
G01P 5/18 (2006.01)
E21B 47/10 (2012.01)
G01F 1/58 (2006.01)
G01N 27/02 (2006.01)
G01V 3/10 (2006.01)

(52) U.S. Cl.
CPC ............... *G01P 5/18* (2013.01); *G01N 27/02* (2013.01); *G01V 3/104* (2013.01)

(56) References Cited

U.S. PATENT DOCUMENTS

| | | | |
|---|---|---|---|
| 6,601,458 | B1 | 8/2003 | Gysling et al. |
| 7,276,916 | B2 | 10/2007 | Hammer |
| 7,875,455 | B1* | 1/2011 | Li .......................... E21B 47/06 422/82.02 |
| 10,378,941 | B2 | 8/2019 | McCann et al. |
| 2003/0020493 | A1 | 1/2003 | Haase et al. |
| 2003/0066359 | A1 | 4/2003 | Gysling et al. |
| 2004/0139791 | A1* | 7/2004 | Johansen ........... G01N 33/2823 73/61.44 |
| 2005/0217350 | A1* | 10/2005 | Jabusch ................ E21B 43/006 73/64.55 |
| 2007/0083340 | A1 | 4/2007 | Bailey et al. |
| 2007/0157737 | A1 | 7/2007 | Gysling et al. |
| 2008/0258717 | A1 | 10/2008 | Igney et al. |
| 2011/0112773 | A1* | 5/2011 | Atkinson ................ G01F 1/663 702/47 |
| 2011/0138928 | A1 | 6/2011 | Xie et al. |
| 2011/0259120 | A1 | 10/2011 | Thonstad |
| 2012/0038368 | A1 | 2/2012 | Mahalingam et al. |
| 2012/0185220 | A1 | 7/2012 | Shippen |
| 2013/0036817 | A1 | 2/2013 | Lucas et al. |
| 2013/0144548 | A1* | 6/2013 | Xie .......................... G01F 1/60 702/65 |
| 2014/0137642 | A1 | 5/2014 | Henry et al. |
| 2014/0253116 | A1* | 9/2014 | Freedman ............... G01R 33/30 324/303 |
| 2016/0245073 | A1 | 8/2016 | Hansen et al. |
| 2019/0310120 | A1 | 10/2019 | McCann et al. |

FOREIGN PATENT DOCUMENTS

| | | |
|---|---|---|
| GB | 2 019 558 A | 10/1979 |
| GB | 2 390 683 A | 1/2004 |
| JP | H08271469 A | 10/1996 |
| WO | WO 2007/089412 A2 | 8/2007 |
| WO | WO 2008/011649 A1 | 1/2008 |
| WO | WO 2008/069695 A2 | 6/2008 |
| WO | WO 2010/071447 A1 | 6/2010 |
| WO | WO 2010/145851 A1 | 12/2010 |
| WO | WO 2011/005133 A1 | 1/2011 |
| WO | WO 2011/119045 A1 | 9/2011 |
| WO | WO 2011/128656 A1 | 10/2011 |

OTHER PUBLICATIONS

Examination Report under Section 17 & 18(3) from GB1319517.7, dated Dec. 2, 2013.
Examination Report under Section 18(3) from GB1319517.7, dated Aug. 21, 2014.
Examination Report under Section 17 & 18(3) from GB1319515.1, dated Dec. 11, 2013.
Examination Report under Section 18(3) from GB1319515.1, dated Nov. 30, 2015.
Examination Report under Section 18(3) from GB1319515.1, dated Nov. 6, 2014.
Notification of Grant: Patent Serial No. GB 2513679, dated Dec. 8, 2015.
Thorn, R., et al., "Three-Phase Flow Measurement in the Petroleum Industry," Measurement Science and Technology, IOP, vol. 24, No. 1, p. 12003, (17 pp), Oct. 29, 2012.
Wang, J. Z., et al., "Numerical Simulation Modelling for Velocity Measurement of Electromagnetic Flow Meter," Journal of Physics: Conference Series, Inst. of Physics Publishing, vol. 48, No. 1, pp. 36-40, Oct. 1, 2006.
Xiang, Deng, et al., "Theoretical Study of Vertical Slug Flow Measurement by Data Fusion from Electromagnetic Flowmeter and Electrical Resistance Tomography," Flow Measurement and Instrumentation, vol. 22, No. 4, pp. 272-278, Mar. 15, 2011.
Ziqiang, Cui, et al., "An Integrated ECT/ERT Dual Modality Sensor," 2009 IEEE Instrumentation and Measurement Technology Conference, Singapore, May 5-7, 2009, pp. 1434-1438, May 5, 2009.
Xiang, Deng, et al., "Fusion Research of Electrical Tomography with Other Sensors for Two-Hase Flow Measurement," Measurement Science Review, vol. 12, No. 2, Apr. 19, 2012.
Notification of Transmittal of the International Search Report and the Written Opinion of the International Searching Authority, PCT/EP2014/058907, dated Sep. 3, 2014.
Ballester, P. J. and Carter, J. N., "Model Calibration of a Real Petroleum Reservoir Using a Parallel Real-Coded Genetic Algorithm," IEEE Congress on Evolutionary Computation, Singapore (Sep. 25-28, 2007).
Cheng, C.-T., et al., "Multiple Criteria Rainfall-Runoff Model Calibration Using a Parallel Genetic Algorithm in a Cluster of Computers," *Hydrological Sciences Journal*, 50(6):1069-1087 (2005).
Guet, S.C.L., "Bubble Size Effect on the Gas-Lift Technique," *DUP Science* (Delft University Press), (2004).
Kennedy, M.C., et al., "Bayesian Calibration of Computer Models," *J. R. Statist. Soc. B.*, 63(Part 3):425-464 (2001).
Lødøen, O. P., et al., "Bayesian Calibration of Hydrocarbon Reservoir Models Using an Approximate Reservoir Simulator in the Prior Specification," *Norwegian University of Science and Technology*, pp. 1-21 (2005).
Wilding, E., "Creating a System to Analyze Air Bubbles in Liquid," *National Instruments*, [online], [retrieved on Oct. 29, 2015], Retrieved from the Internet URL: http://sine.ni.com/cs/app/doc/p/id/cs-350.
Wilkinson, R.D., "Bayesian Calibration of Expensive Multivariate Computer Experiments." in *Computational Methods for Large-Scale Inverse Problems and Quantification of Uncertainity*, John Wiley & Sons, Ltd., eds: (People on Earth) (2001).
Hunt, A., "Is Electrical Capacitance Tomography Ready for Oilfield Application?," SCADA 2012, Total SA, Pau France. Jun. 13-14, 2012.
"Conductivity (Electrolytic),"Wikipedia page, from: http://en.wikipedia.org/wiki/Conductivity_(electrolytic) [retrieved on May 15, 2019].
"Conductivity Sensors," from http://www.abb.com/product/us/9AAC100018.aspx [retrieved on May 15, 2019].

(56) References Cited

OTHER PUBLICATIONS

"Theory and Application of Conductivity," Emerson Process, Management, Jan. 2010, from: http://www2.emersonprocess.com/siteadmincenter/PM%20Rosemount%20Analytical%20Documents/Liq_ADS_43-018.pdf [retrieved on May 15, 2019].

A Non Final Office Action for US. Appl. No. 16/450,961, entitled: Method And Apparatus For Monitoring The Flow Of Mixtures Of Fluids In A Pipe, dated Oct. 30, 2019.

Notice of Allowance for U.S. Appl. No. 16/450,961, entitled: Method and Apparatus for Monitoring the Flow of Mixtures of Fluids in a Pipe, dated Apr. 6, 2020.

* cited by examiner

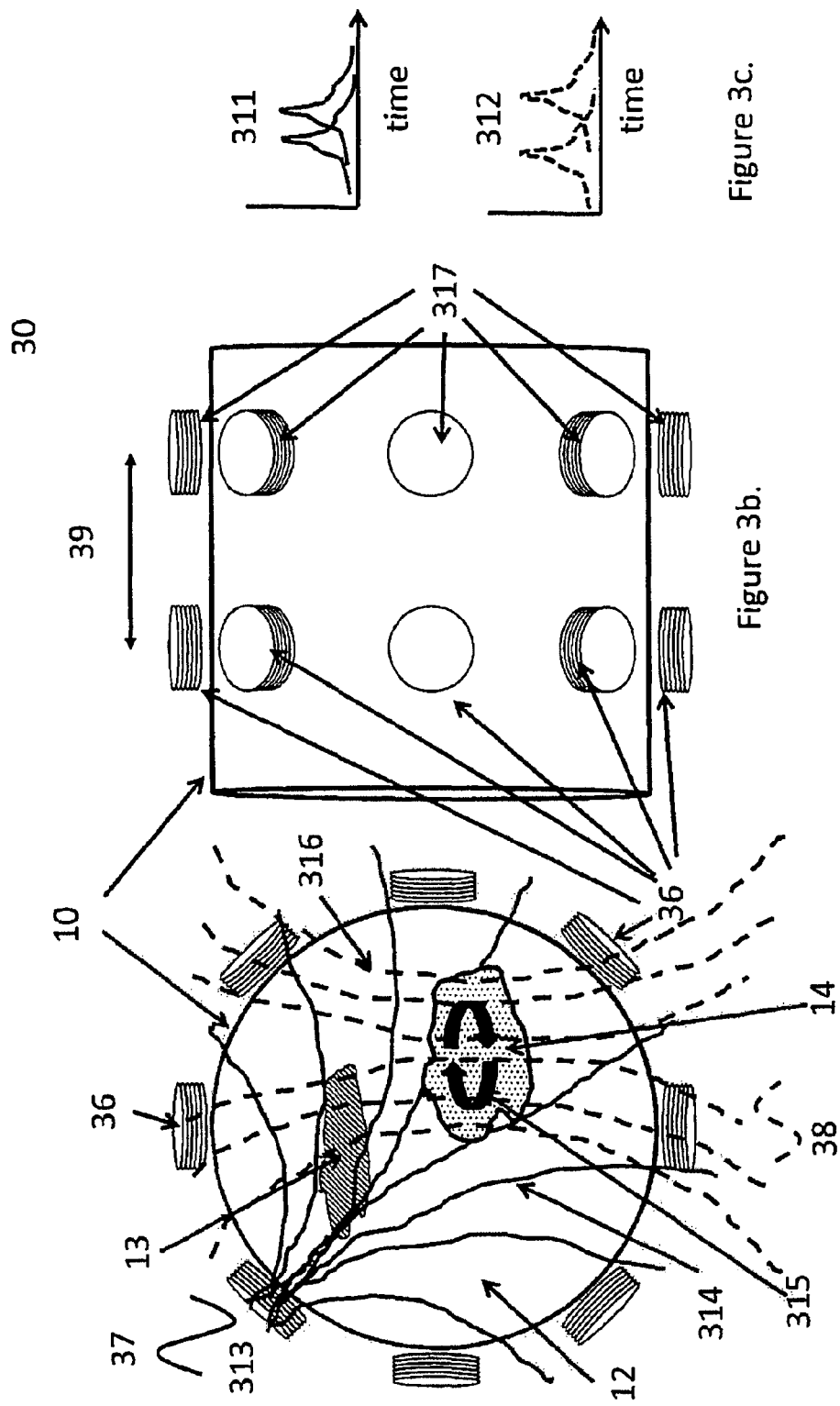

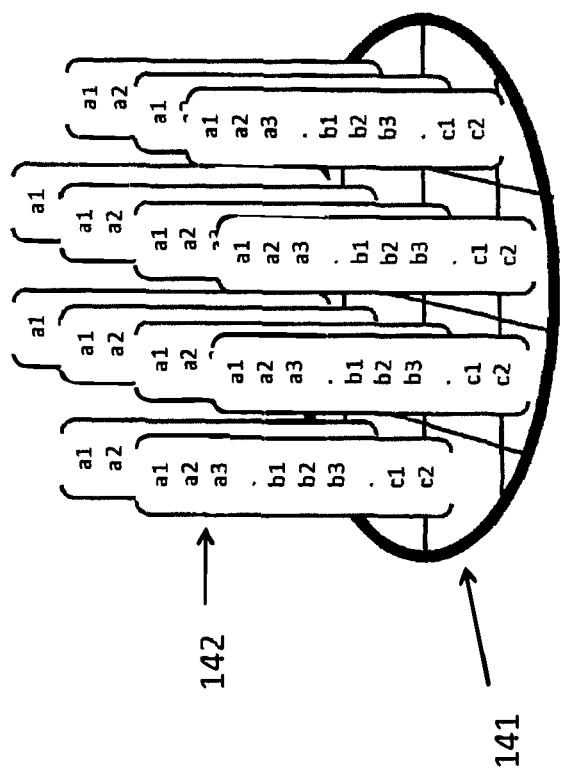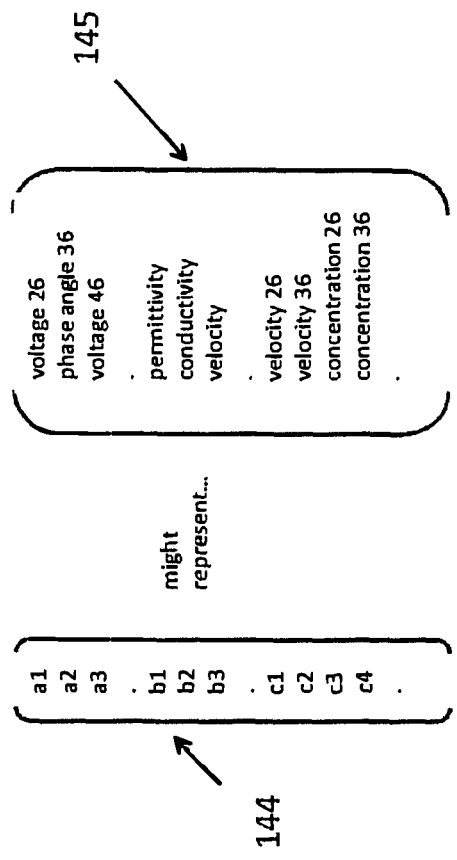
Figure 14

METHOD AND APPARATUS FOR MONITORING THE FLOW OF MIXTURES OF FLUIDS IN A PIPE

RELATED APPLICATIONS

This application is a continuation of U.S. application Ser. No. 14/888,019, which is the U.S. National Stage Application of International Application No. PCT/EP2014/058907, filed on Apr. 30, 2014, published in English, which claims priority under 35 U.S.C. § 119 or 365 to Great Britain Application No. 1307785.4, filed on Apr. 30, 2013. The entire teachings of the above applications are incorporated herein by reference.

This invention relates to a multiphase flow metering device and applications thereof, in particular within the oil and gas exploration and production industry.

In the current state of the art the optimization of production from subsea wells is difficult because flow from multiple wells is often commingled in subsea manifolds and transferred to surface through a single flowline. As a result, the flow from any one well is not measured and so cannot be optimized by means of artificial lift or other techniques. For example, if there is an increase in the production of water at surface then it is unknown from which well it is coming. The multiphase flowmeters in the market today are expensive and may not be reliable enough to be placed on each wellhead.

Multi-component flows are often loosely called multiphase. For example, a mixed flow of oil and water is not multiphase (it is one phase—liquid) but it is multi-component (two components—oil and water). A typical oilfield flow of oil, gas and water may often contain solids (for example, sand or hydrates) and thus have four components but only three phases. Throughout this specification, the same loose convention as in many industries is adopted and the terms multi-component and multiphase are used interchangeably to mean the same thing—a mixture of fluids and solids flowing in a pipe.

In the case of a multiphase flow with several components, the operator (for example, an oil company) requirement may be the volume or mass flowrate of some or all of components. In a typical oilfield flow the operator requires the measurement of the mass flow of gas, oil and often the water, but typically not specifically the solids. Although measurement of the flowrate or concentration of solids is a useful additional measurement and can help determine the health of the downhole sand screens or gravel packs. Early detection of the potential failure of these elements of the system will help reduce failure of other components due to, for example, erosion.

There are many applications of multiphase flowmeters in the oil industry for flows of gas, oil, water and solids: downhole, wellhead, platform, pipelines, subsea, wet gas, heavy oil, gas lift, tar sands etc. The further upstream in the process the more complex and demanding the conditions, so subsea and downhole are the most difficult.

An oil well starts life producing mainly oil, but as the oil depressurizes along the flow line gas is liberated, so at the wellhead there is almost always some gas present. In addition, most wells produce some water and the amount increases through the life of the well until by the end of its life the well may be producing mostly water. Because of the long flow path even small quantities of gas may cause the well to slug—oscillating between high liquid and high gas states.

A gas well starts life producing mainly gas, but frequently this is associated with the production of light oil known as condensate and again later in life some water is likely to be produced.

Therefore both oil and gas wells generate multiphase flows with gas, oil and water almost always present in highly variable quantities, and in addition many reservoir formations produce sand as a natural part of production, and any workover of the reservoir will often leave some solids to be cleaned out over the succeeding days or weeks.

In this specification and claims the term 'oil well' will be used to represent any kind of well drilled for oil and gas exploration and/or production, including injection wells that can be used for the purposes of production enhancement.

It is very beneficial for both the reservoir and production engineers to have reliable measurements of the multiple phases in the production from a well. In addition to the quantitative measurements of the volume or mass flowrates of the individual components, it is also very beneficial to determine the flow regime, that is, how the different phases are distributed in the flow. For example, the same volume of gas arriving at surface as slugs rather than evenly distributed in the flow represents very different production scenarios and poses different problems to the production engineer. Real-time determination of these different and changing flow regimes would offer reservoir and production engineers a deeper insight into production and so allow improved optimization.

The historical 'normal' method for measuring flowrate of oil, gas and water is to use a separator that separates the input flow into output flows of oil, gas and water with three independent single-phase flowmeters to measure each. In production this is still the prime measurement technique—here the flow needs to be separated anyway for use in the downstream process. For well testing, well monitoring and subsea completions however the separator is a large, expensive and not very accurate unit and is steadily being replaced by multiphase flowmeters. However, as already mentioned, multiphase flowmeters available in the market have many drawbacks that have limited their application and the invention here disclosed addresses these shortcomings. In particular, multiphase flowmeters on the market today widely use a nuclear source (sometimes more than one) and restrict the flow by the use of a Venturi element to the meter.

The oilfield environment is physically demanding—high pressure (up to 1000 bar), with high temperatures of the fluids (up to 250 degrees Celsius), variation of physical properties of the oil and gas (PVT), variation in salinity of the produced water, issues of $H_2S$ production (known as sour gas), subsea or downhole access etc. This has led to various meter designs involving multiple technologies in order to address each challenge. As a result the cost base is high, independent of the technologies used.

A list of the main multiphase flowmeters available can be found in oil industry catalogues (see for example MPFM Handbook Revision2 2005 ISBN-82-91341-89-3) along with the technologies used in each. The essence of many of them is that the overall mass flow is estimated by a Venturi meter, in most the density is estimated using a gamma density meter and then some sort of electrical method is used to estimate the oil/water ratio. The common use of a gamma ray nuclear source is one particular requirement of devices that the industry has wanted to remove for sometime. Obviously the use of a nuclear source brings issues related to health and safety but also security in some situations. The common use of a Venturi has also lead to reliability issues. This is due to the fact that the pressure in the meter can be very high (1000s of PSI) but pressure drop across the Venturi is typically less than 0.1 PSI. As a result it is typical to have a delta pressure (dP) sensor rather than two absolute pressure sensors, one each side of the Venturi. It should also be noted that the Venturi imposes a restriction in the flow. Unfortunately, dP sensors can be a source of reliability issues, for example, a blockage or restriction of the pressure feed on one side of the sensor causes an overpressure resulting in the sensor failing. Large pressure transients cross the Venturi can have a similar result. It is not uncommon for these dP gauges to fail within a year or two of operation.

Another issue with solutions in the prior art is the fact that average densities and velocities are generally estimated across the meter, for example, the nuclear absorption provides an average density estimation across the meter. Also, it is well known that in many situations the velocity of the different phases can be quite different, for example, the velocity of the gas bubbles can be very different to the velocity of the oil or water in which they travel. The difference is often called the 'slip velocity' of one phase relative to another. Because the various fluids are highly fluctuating in both space and time, it can be shown that there is an unbounded error if the average phase concentration is multiplied by the average phase velocity to get average phase volumetric flowrate, this error may easily be 50% of the reading, see Hunt 2012. In fact, the phase velocity and concentration must be multiplied together before integration across the flow to get the correct answer. However, generally, current multiphase flowmeters do the multiplication incorrectly because they are based on independent devices that average across the flow first.

Corrections may be attempted by using slip velocity models. However the fundamental problem of the incorrect integration process means that the correction is often large and uncertain.

The only way to reduce the slip velocity to zero is to completely homogenize the different phases before metering but this would necessitate significant separation problems downstream, otherwise accurate multiphase flowrate measurements must start with independent estimates of velocity and concentration of each component across the flow.

Another issue with the solutions presently available is that phase concentrations are averages and it is unknown how these phases are distributed in the flow. For example, a meter may indicate that the flow stream contains 70% oil and 30% gas. However, it is not necessarily known if the gas is distributed in small bubbles in the stream or in larger bubbles or even a single bubble.

Finally, some prior art has attempted to address some of these issues, for example, see EP 2379990 A1 Multiphase flowmeter. However, the resulting solution involves splitting the flow such that the meter has an obstruction in the flow stream. In many applications the measurement must be non-intrusive so that access to the pipeline is not impeded. The addition of an obstruction in the meter has significant disadvantages. For example, anything directly in the flow path has a tendency to erode, leading to early failure. The increased pressure drop can also impact production performance.

Three-phase flow has nine variables: the velocity, density and concentration (often call holdup) of each phase. If the pipe contains only the three phases then the sum of concentrations=100%. Therefore, in principle eight measurements are required. In instruments available today there are generally less than 8 measurements (often using different technologies) and so assumptions are required. For example, phase densities are measured using samples of fluids and are considered constant between samples, slip velocities are calculated using models or all phases are pre-mixed before passing through the meter and it is assumed all 3 velocities are equal. Any of these assumptions can introduce significant errors in the measurements obtained.

It is understood that electromagnetic energy can provide information related to certain physical properties of materials exposed to this type of energy. Well known examples include the electromagnetic flowmeter, electrical capacitance tomography (ECT), electrical resistance tomography (ERT) and magnetic inductance tomography (MIT). In each case a varying electric or magnetic field can be applied across the material and measurements of voltage, current and magnetic field can be used to measure certain physical parameters of the constituent components.

Applications of such techniques to measure multiphase flows are well known, for example an imaging electromagnetic flowmeter (IEF) is disclosed in WO/2011/128656 A1 to measure the velocity of the conducting component of a multiphase flow, and a system for measuring the flowrate of non-conducting multiphase flows in disclosed in GB2390683. However, these techniques are limited in their applications and cannot be used alone to provide a complete multiphase flowmeter as neither has the ability to provide a multiphase flowmeter that can provide measurements with a broad enough range of oil/water/gas/solids concentrations commonly found in oil and gas operations.

Another electromagnetic interrogation method that has been used in the medical industry is MIT (Magnetic Induction Tomography). The principle of this measurement is that electric coils are excited with alternating current that results in the coils producing varying magnetics fields. The object of interest is placed within these fields and the varying field induces varying currents within the object that is dependent on the conductivity of the object. The varying currents in the object produce secondary magnetic fields that can be received by the same or other coils. The received secondary magnetic field in conjunction with the primary imposed magnetic field can use be used to compute the conductivity contrast between the object and the material that surrounds it. See for example EP 2044470 A1 and US 20080258717. Magnetic induction has been used to measure components of a multiphase flow, see U.S. Pat. No. 7,276,916B2, but this application makes only one measurement across the flow. The present invention aims at least partially to provide technical solutions to the above restrictions associated with the technology presently used in the oil and gas industry.

In particular, present invention aims at least partially to provide a monitoring apparatus and method which can (i) measure the multiphase flow from any one well to enable the flow to be optimized, for example by means of artificial lift or other techniques; and/or (ii) enable the determination of from which well water is coming in the event of an increase in the production of water at the surface; and/or (iii) provide an inexpensive and reliable multiphase flowmeter which can make it commercially and technically feasible to install a multiphase flowmeter on each wellhead of a multiple wellhead oilfield system.

The present invention also aims at least partially to provide a monitoring apparatus and method which can provide a multiphase fluid flow measurement which is highly precise in space and time and can be directly linked in a real-time manner to reservoir or production conditions, in order to provide real-time monitoring, and optional control, of the production parameters, and imaging of multiphase flow structures and analysis of multiphase flow structures in real-time or as a playback.

The present invention also aims at least partially to provide a monitoring apparatus and method which avoid the need for a multiphase fluid flow measurement device employing a nuclear source or a low reliability dP gauge as employed in current known multiphase fluid flow measurement devices.

The present invention also aims at least partially to provide a monitoring apparatus and method which can provide accurate multiphase flowrate measurements with independent estimates of velocity and concentration of each component across the flow which can determine the slip velocity. This can obviate the need in the current state of the art to modify the flow to reduce the slip velocity to zero, which would require to completely homogenize the different phases before metering and necessitate significant separation problems downstream.

The present invention also aims at least partially to provide a monitoring apparatus and method which can readily provide information concerning non-averaged information with respect to phase concentrations and the distribution of the phases in the multiphase fluid flow, such information being important to the production operations and optimization of the oil and gas production system.

The present invention also aims at least partially to provide a monitoring apparatus and method which can employ a non-intrusive meter with full bore access which does not incorporate a flow restrictor such as a venturi.

According to a first aspect of this invention, there is provided a monitoring apparatus for monitoring a multiphase flow in a pipe, the apparatus comprising:
a. a first monitoring module coupled to the pipe and adapted to provide first output data representing a respective concentration of one phase of a plurality of phases, or a mixture of at least two of the phases, in the multiphase flow by processing at least one first variable representing electrical permittivity of one phase or a mixture of at least two of the phases of the multiphase flow;
b. a second monitoring module coupled to the pipe and adapted to provide second output data representing a respective concentration of one phase, or a mixture of at least two of the phases, of the plurality of phases in the multiphase flow by processing at least one second variable representing electrical conductivity of one phase or a mixture of at least two of the phases of the multiphase flow; and
c. a third monitoring module coupled to the pipe and adapted to provide third output data representing a respective velocity of at least one phase of the plurality of phases in the multiphase flow by processing at least one third variable representing velocity of at least one of the phases, wherein each of the first, second and third monitoring modules is adapted respectively to provide the first, second or third output data in a form representing the respective first, second or third variable across at least a portion of the cross-sectional area of an interior of the pipe; and
d. a processing system for processing the first, second and third data to combine the first, second and third data to provide combined data representing all constituents of the multiphase flow across at least the portion of the cross-sectional area of an interior of the pipe.

According to a second aspect of this invention, there is provided a method of monitoring a multiphase flow in a pipe, the method comprising the steps a to c, which are carried out in any order, of:

a. obtaining first data related to at least one first variable representing electrical permittivity of at least one phase of a plurality of phases, or a mixture of at least two of the phases, in the multiphase flow and processing the first data to provide first output data representing a respective concentration of one phase or a mixture of at least two phases of the phases in the multiphase flow;
b. obtaining second data related to at least one second variable representing electrical conductivity of one phase, or a mixture of at least two of the phases, of the plurality of phases in the multiphase flow and processing the second data to provide second output data representing a respective concentration of one phase or a mixture of at least two phases of the plurality of phases in the multiphase flow; and
c. obtaining third data related to at least one third variable representing velocity of at least one phase of the plurality of phases in the multiphase flow and processing the third data to provide third output data representing a respective velocity of at least one phase of the plurality of phases in the multiphase flow,
the method further comprising the steps of:
d. providing each of the first, second or third output data in a form representing the respective first, second or third variable across at least a portion of the cross-sectional area of an interior of the pipe; and
e. processing the first, second and third data to combine the first, second and third data to provide combined data representing all constituents of the multiphase flow across at least the portion of the cross-sectional area of an interior of the pipe.

According to a third aspect of this invention, there is provided an oil well system including a plurality of oil wells, a plurality of collection pipelines, and a manifold, each oil well having a respective collection pipeline connected to the manifold, a common output pipeline extending from the manifold to an oil collection assembly, monitoring apparatus for monitoring a multiphase flow in a pipe, the monitoring apparatus being coupled to a pipe comprising a collection pipeline or a common output pipeline, and being adapted to provide output data representing (a) a respective concentration of one phase of a plurality of phases, or a mixture of at least two of the phases, in the multiphase flow, (b) a respective electrical conductivity of one phase or a mixture of at least two of the phases of the multiphase flow; and (c) a respective velocity of at least one phase of the plurality of phases in the multiphase flow, the monitoring apparatus comprising:
a. a first monitoring module coupled to the pipe and adapted to provide first output data representing a respective concentration of one phase of a plurality of phases, or a mixture of at least two of the phases, in the multiphase flow by processing at least one first variable representing electrical permittivity of one phase or a mixture of at least two of the phases of the multiphase flow;
b. a second monitoring module coupled to the pipe and adapted to provide second output data representing a respective concentration of one phase, or a mixture of at least two of the phases, of the plurality of phases in the multiphase flow by processing at least one second variable representing electrical conductivity of one phase or a mixture of at least two of the phases of the multiphase flow; and
c. a third monitoring module coupled to the pipe and adapted to provide third output data representing a respective velocity of at least one phase of the plurality of phases in the multiphase flow by processing at least one third variable representing velocity of at least one of the phases, wherein the first monitoring module is adapted to provide the first output data in a form representing the concentration or density of at least one or each of the phases, the second monitoring module is adapted to provide the second output data in a form representing the density or concentration of at least one or each of the phases and the third monitoring module is adapted to provide the third output data in a form representing the velocity of at least an aqueous phase or each of the phases, to provide the first, second and third output data in a form representing the concentration, density and velocity of each of the phases, a control system including a multiphase fluid flow model, and a data connection between the or each monitoring apparatus and the control system to enable the output data to be input to the multiphase fluid flow model.

According to a fourth aspect of this invention, there is provided a method of operating an oil well system including a plurality of oil wells, a plurality of collection pipelines, and a manifold, each oil well having a respective collection pipeline connected to the manifold, a common output pipeline extending from the manifold to an oil collection assembly, monitoring apparatus for monitoring a multiphase fluid flow in a pipe, the monitoring apparatus being coupled to a pipe comprising a collection pipeline or a common output pipeline extending from the manifold to an oil collection assembly, the method comprising the steps of:

a. operating the monitoring apparatus to provide output data, associated with the pipe, representing (a) a respective electrical permittivity of one phase of a plurality of phases, or a mixture of at least two of the phases, in the multiphase fluid flow, (b) a respective electrical conductivity of one phase or a mixture of at least two of the phases of the multiphase fluid flow; and (c) a respective velocity of at least one phase of the plurality of phases in the multiphase fluid flow, wherein the multiphase fluid includes at least two of mineral oil, natural gas and water and the output data are processed to determine, at least one position across the cross-section of the pipe, (a) the individual concentration of at least one of natural gas, mineral oil and/or water, (b) the individual density of at least one of natural gas, mineral oil and/or water and (c) the individual velocity of at least one of natural gas, mineral oil and/or water, b. inputting the output data to a multiphase fluid flow model of a surface control system, to calibrate or modify the multiphase fluid flow model; and c. using the calibrated or modified multiphase fluid flow model to monitor and/or control the operation of the oil well system.

According to a fifth aspect of the invention there is provided a method of defining a multiphase flow comprising three phases, the method comprising measuring, directly or indirectly, at least one position across the cross-section of the flow, (a) the individual concentration of each of the three phases to provide first data; (b) the individual density of each of the three phases to provide second data and (c) the individual velocity of each of the three phases to provide third data, wherein the measured concentration, density and velocity values of the three phases constitute nine parameters representing the multiphase flow, and processing the first, second and third data to combine the first, second and third data to provide combined data representing all constituents of the multiphase flow across at least a portion of the cross-sectional area of the flow.

The preferred embodiments of the present invention can provide a non-intrusive device for multiphase flow measurements that is completely electromagnetic, for example, does not require a nuclear source or a Venturi.

Additionally, the preferred embodiments of the present invention can provide that the device can provide individual flowrates of the constituent components of the flow. Preferably the flow consists of more than two individual constituent fluids such as oil, gas or water. Additionally, the flow can contain solids, e.g., sand.

The preferred embodiments of the present invention can provide a number of electrodes and/or coils, functioning as antennae, that are placed around the circumference of the pipeline, preferably in a ring configuration, but another geometrical arrangement could alternatively be employed.

The preferred embodiments of the present invention can provide that each antenna can be a transmitter or receiver or can be both a transmitter and receiver of electromagnetic signals. At least one transmitter and one receiver are required. Preferably a plurality of both transmitters are receivers are provided whose number can be arranged to maximize the coverage or optimized for a specific application, e.g., a greater number of measurements sensitive to water can be place on the bottom of the pipe and/or a greater number sensitive to gas can be place along the top of the pipe.

The preferred embodiments of the present invention can provide that the electromagnetic signals generated and transmitted can be of any form, alternating or steady. Preferably they are regularly varying sine waves or square waves.

The preferred embodiments of the present invention can provide that each antenna can be an electrode or a coil or a combination of both. Additionally, the antennae can be of any shape to best suit the implementation but preferably they can be circular or square or rectangular in shape. Additionally, antennae such as coils may enclose other antennae or the entire set of other antennae.

The preferred embodiments of the present invention can provide that some antennae can be electrically insulated from the fluid flowing through the device and/or some can be in electrical contact with the flow.

The preferred embodiments of the present invention can provide a device that uses the combination of Electrical Capacitance Tomography (ECT) and/or Imaging Electrical Flowmeter (IEF) and/or Magnetic Induction Tomography (MIT). Additionally, the device can be a combination of ECT and/or IEF and/or MIT and/or Electric Resistance Tomography (ERT) and/or Electric Inductance Tomography (EIT).

The preferred embodiments of the present invention can provide a device that has multiple sets of antennae preferably arranges as rings around the circumference and separated by a known distance along the axis of the pipe.

The preferred embodiments of the present invention can provide that signal processing is provided that uses the signals transmitted and received by said multiple sets of antennae and performs cross correlation of these signals in order to compute the time of flight of correlated features between the two sets of antennae that are of a known distance apart so that the time of flight and distance can be used to compute the velocity. Preferably each correlated feature represents a different constituent or phase of the flow (oil, water, gas or solids) passing the ring of antennae. More preferably correlations on different antennae can be used to compute a velocity profile for each constituent of the flow both in cross section and axially along the pipe.

The preferred embodiments of the present invention can provide a non-intrusive device that is completely electromagnetic and can be used for oil and gas application and can be deployed; topside, subsea, on pipelines (both subsea and terrestrial) or downhole. Additionally the device can provide individual flowrates of the constituent components of the flow. Preferably the flow consists of more than two individual constituent fluids such as oil, gas or water. Additionally, the flow can contain solids, e.g., sand. Additionally, the device can be constructed of non-conducting composite materials suitable for high pressure and high temperature and erosion and corrosion resistant suitable for conditions experienced in oil and gas applications.

The preferred embodiments of the present invention can provide that signal processing algorithms are provided that use the transmitted and received signals from the antennae to obtain a mesh or grid of fluid properties across the cross section of the pipe. Preferably, the processing produces 2D meshes or grids of the different constituents in the flow (oil, water, gas and solids) through the pipe.

The preferred embodiments of the present invention can provide that signal processing is provided that produces images of the electrical properties that in turn are manipulated to create images of the different constituents in the flow (oil, water, gas and solids) through the pipe. Preferably processing is provided to create 2D images of the different constituents in the flow using different electromagnetic measurements to distinguish between the said different constituents (oil, water, gas and solids) in the flow.

The preferred embodiments of the present invention can provide that software or processing is provided to overlay or integrate or combine multiple 2D meshes, grids or images obtained at the same time to create one mesh, grid or image that contains all constituents of the flow in a single mesh, grid or image representing the cross section of the pipe at that particular time.

The preferred embodiments of the present invention can provide that processing is provided to said combined mesh, grid or image to calculate the density and concentration of the fluid at any point in the cross section. Additionally processing is provided that takes said electrical measurements and converts them directly into a velocity map of the flow, thus providing velocities profiles of each constituent or phase of the multiphase flow.

The preferred embodiments of the present invention can provide that processing is provided that combines said velocity profiles and overlaid images to provide the flowrate per unit area at any point in the cross section.

The preferred embodiments of the present invention can provide that processing is provided that uses fluid property meshes/grids and/or images and/or velocity profiles and maps to calibrate, validate and characterize multiphase flow modelling software, for example, OLGA (which is an industry recognized advanced model, see http://www.sptgroup.com/en/Products/OLGA/), in order to improve their ability to predict flow regimes, how they behave and how they impact production. Preferably such calibrated models are used to improve their ability to help production and reservoir engineers optimize well and field production, which is clearly of significant value to the operator. An example workflow could be; 1) measure flow parameters; 2) input these into a real-time flow model (OLGA); 3) vary flow rates, choke positions, gas lift parameters, ESP (electrical submersible pump) speed etc.; 4) Iterate back to step 1) changing system parameters 3) until the production is optimized.

The preferred embodiments of the present invention can provide processing that records said 2D meshes, grids or images at a regular period of time to create a real-time recording or movie showing all constituents of the flow as they flow past the said multiphase flowmeter device. Additionally, providing 3D images of the flow in the pipe that vary with time, that is, 4D meshes, grids or images. Additionally using such 4D images in a virtual reality environment, e.g., collaborative environments where production and reservoir engineers can interact with said images, along with other information available from other sources, e.g., reservoir information, and better understand the structures in the flow. Additionally, 2D, 3D and 4D meshes, grids and images can be recorded and run in 'play-back' in order to evaluate various production scenarios.

The preferred embodiments of the present invention can provide a database of flow regime characteristics and pattern recognition/matching algorithms to automatically determine flow regime (e.g., bubble, wavy, stratified, annular, plug, slugging etc.) from real-time and recorded meshes/grids and/or images and the transition of those meshes, grids or images. Additionally, such processing will provide real-time indication of flow regimes or the ability to replay recorded information to better understand those flow regimes and how they develop. Additionally, such processing can provide a capability to allow continued analysis of such flow regimes by experts so that the database can be augmented and improved continually.

The preferred embodiments of the present invention can provide a non-intrusive device for multiphase flow measurements that is completely electromagnetic for use in oil and gas to:

Quantify the mass/volume flowrate of different constituents of the flow: oil, water and gas from a well or group of wells Additionally, quantify the mass/volume flowrate of solids, e.g., sand, from a well or group of wells.

Automatically detect and provide warnings of slugging of gas or water in an oil flow.

Automatically determine the trending of the different constituents of the flow from a well or groups of wells, e.g., water production or solids production. Where increasing solids production can provide early warning of sand screen or gravel pack failure and can help minimize erosion of pipelines and other infrastructure.

Provide real-time images and recording of the distribution of the constituents in the multiphase flow from a well or group of wells.

Automatically determine the flow regime continuously and in real-time; for example, slugging, bubbly, wavy, annular, plug, stratified, mist etc.

Detect and quantify reverse flow whereby some constituents are flowing in the opposite direction to the main flow, e.g., water or solids along the bottom of an inclined pipe.

Compute appropriate process control parameters for management of production, e.g., capture and safe handling of gas slugs, removal of solids (e.g., sand) from the flow and separation of oil/gas/water from multiphase flow.

Provide real-time images or meshes/grids of waters of differing salinity, e.g., distinguishing between water that is produced from a formation (connate water) and water that was pumped into offset wells to enhance oil recovery. Additionally, distinguishing between water produced from different reservoirs and so determining the origin of such water.

Determining and showing the distribution of inhibitors or chemicals injected into, e.g., subsea flowlines. For example, corrosion, hydrate, wax inhibitors in order to better control their introduction into the flowline, as an example, their placement and pump rate.

Detect the buildup of hydrates or wax or other deposits at the measurement instrument location.

Track the passage of pigging devices or injected balls, plugs or darts, which can show the start and end of different slugs of fluids so that they can be treated independently.

Monitoring and optimization of heavy oil production in order to tune heating and diluent levels in surface or subsea pipelines to achieve efficient production viscosity of crudes.

Optimize the gas feed rate for gas lift operations, e.g., to prevent gas channel flow which impacts the efficiency of the gas lift systems and thus production performance.

Determine and showing the distribution of solids such as proppant in fracturing operations and other solids pumped, e.g., cement during cementing operations, in order to optimize deployment and usage of such materials.

Monitor the 'flow-back' fluids from fracturing by monitoring their density and/or salinity and/or other fluid properties extracted from the meshes/grids or images produced.

These various aspects of the preferred embodiments of the invention relate to the design and manufacture of a unique imaging-based multiphase flow meter and others relate the processing and analysis of measurements or images produced. The applications of such a meter provides a better understanding of the flow of different fluid phases flowing from a well or reservoir. Real-time images provide the production or reservoir engineer with a unique insight into how a well or reservoir is performing. Such an instrument also removes the need for a nuclear source and a restriction in the flow due to the use of a venturi, both of which are common requirements for instruments in the market today.

The preferred embodiments of this invention disclose a method to measure the flow of mixtures of fluids from a well or group of wells during oil and gas exploration, production or transportation operations. Through these listed aspects of this invention, the inventors have provided different embodiments, which cover some of the potential applications of the multiphase flowmeter described. However, it is understood that this is a subset of the potential applications and those skilled in the art will appreciate that there can be many others which are additionally provided in this invention.

These and other aspects of the present invention will now be described, by way of examples, with reference to the accompanying drawings, in which:

FIGS. 3a, 3b and 3c show schematics of another electromagnetic measurement that is in accordance with another embodiment of the present invention;

FIG. 14 shows a schematic view of state vectors associated with each element of an array or matrix of interpreted measurements;

Hereinafter, the present invention will now be described in more detail with reference to the accompanying figures, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art.

Figure 1:
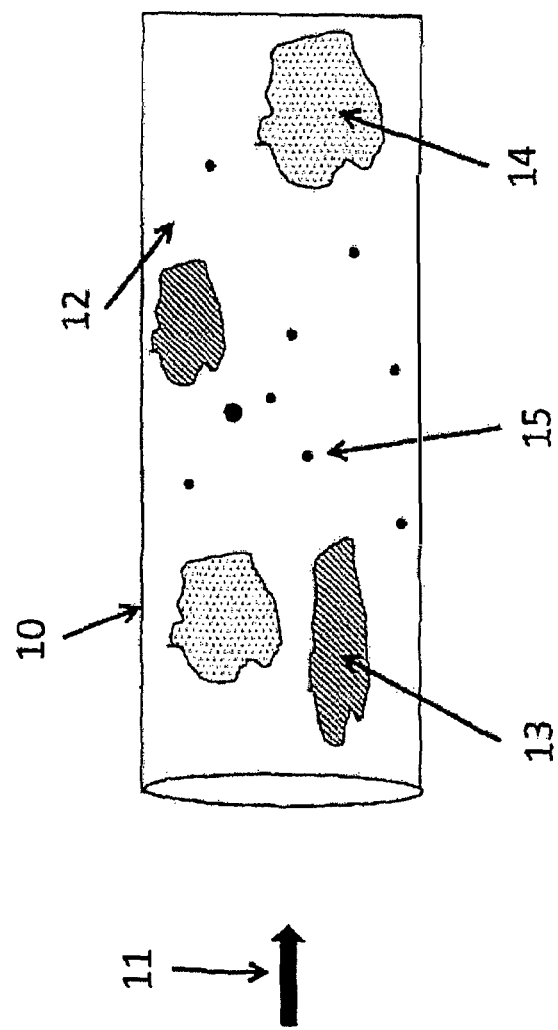
FIG. 1 illustrates multiphase flow through a pipeline.

Referring to FIG. 1 there is shown a schematic of a multiphase flow, 11, in a pipeline 10. In FIG. 1, 12, illustrates the primary or continuous phase of the flow, e.g., oil, water or gas. Within this primary phase there is schematically shown two other constituents to the flow labelled 13 and 14. Solid (e.g., sand) in the flow is illustrated as labelled 15. The figure illustrates that the flow in the pipeline, 10, has multiple phases including solids. Clearly this figure is a simplistic and the distribution of these phases can vary significantly depending on the concentrations of each phase and the flow regime. The structure of such multiphase flows can be very complex and there are many industry papers that attempt to explain this complexity and better understand these various flow regimes, the reasons for their existence and how they affect overall production performance, see for example Hunt et al 2010. However, today there are no multiphase flowmeters that can provide complete details of the flow structures or how they develop. All flowmeters available provide average measurements and additionally they have significant inherent uncertainty in the quantitative values they provide. The invention here described address these and other shortcomings in the solutions available today as described earlier, particularly the requirement for nuclear sources and the requirement for a Venturi.

Overall the described solution combines various electromagnetic measurement techniques and sophisticated processing in order to provide both detailed flow structure and also improved quantitative measurements on the different phases or constituents that make up the multiphase flow. The resultant device is a non-intrusive completely electromagnetic instrument with many features that improve the understanding of multiphase flow measurements.

Figures 2A, 2B, 2C:
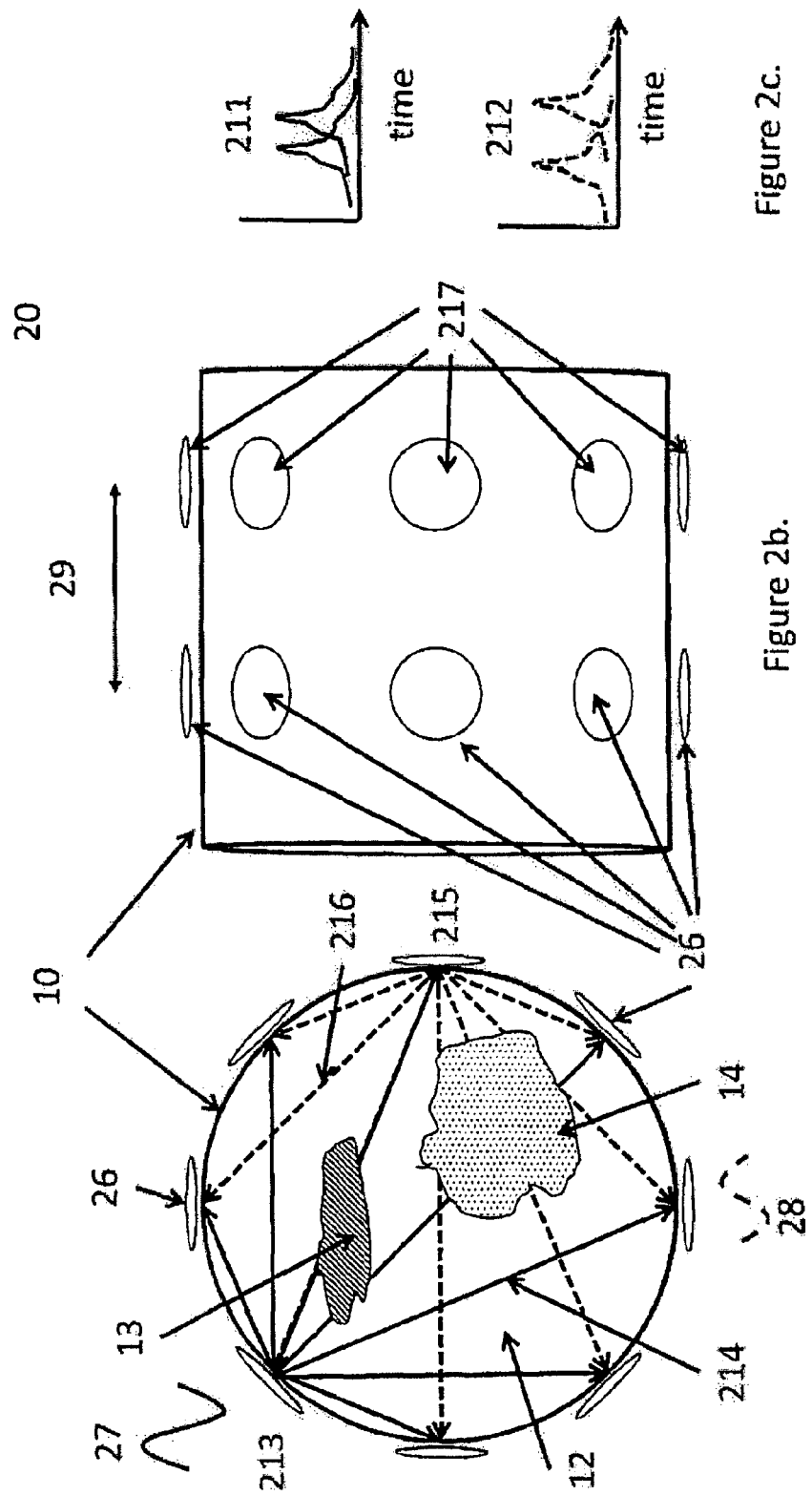
FIGS. 2a, 2b and 2c show schematics of one electromagnetic measurement that is in accordance with an embodiment of the present invention.
Figure 10:
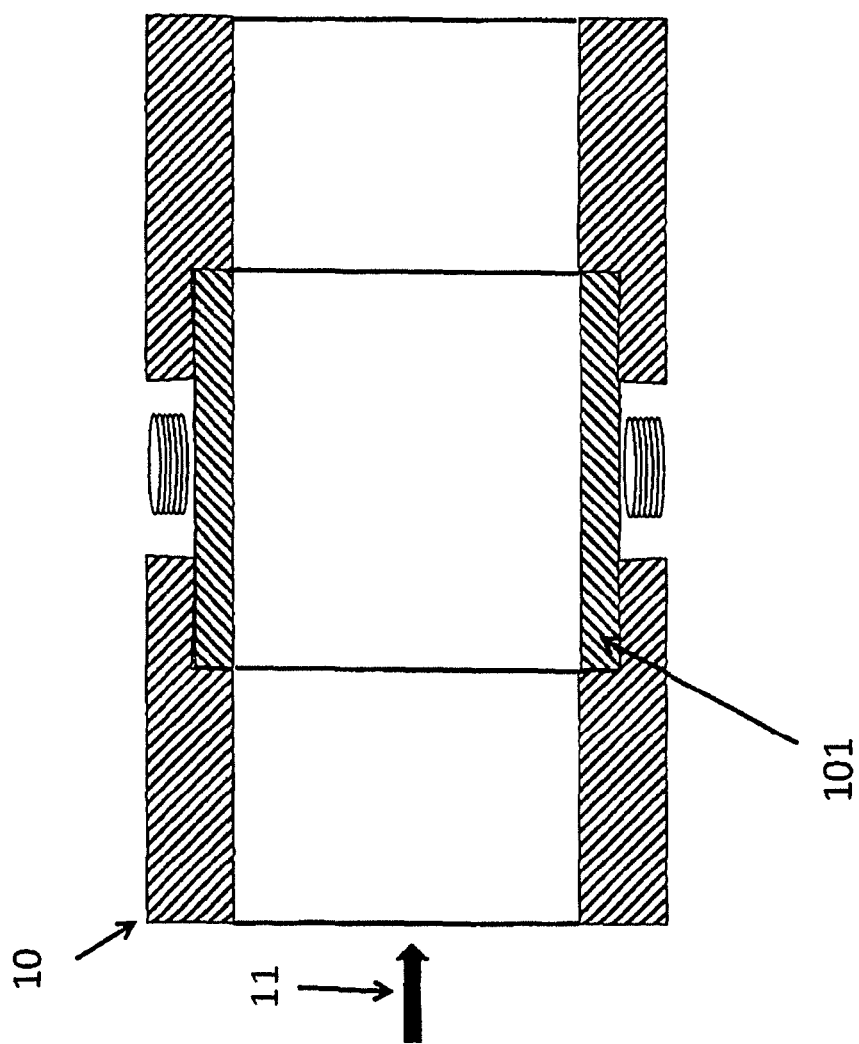
FIG. 10 illustrates an antennae configuration that is in accordance with other embodiments of this invention.
Figure 11:
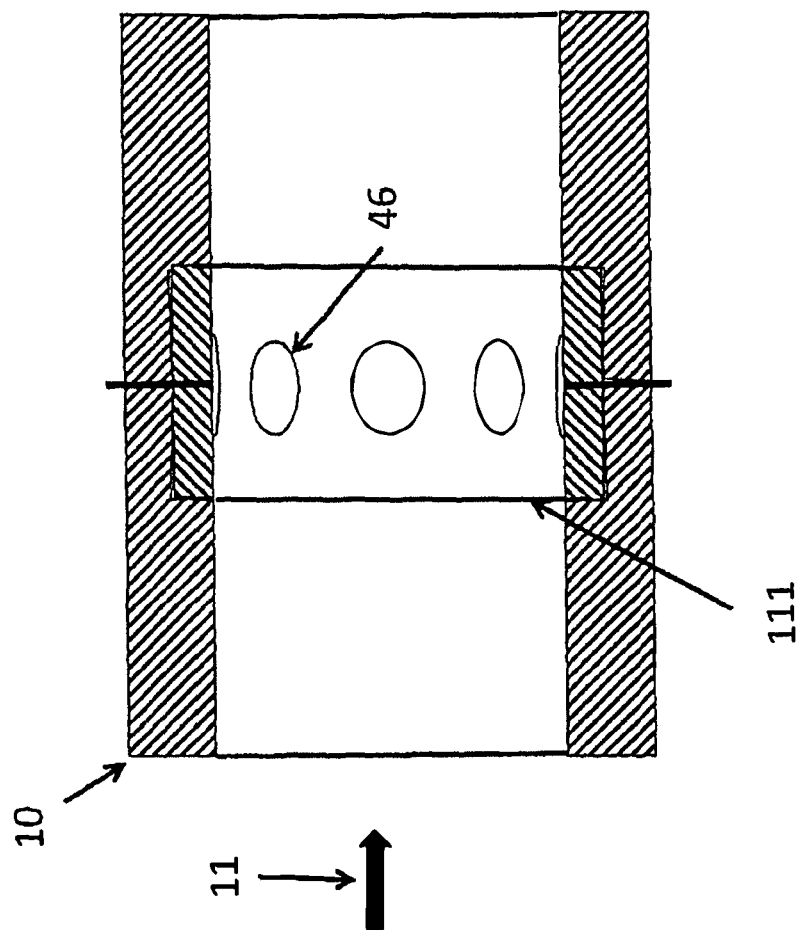
FIG. 11 illustrates yet another antennae configuration that is in accordance with other embodiments of the present invention.
Figure 12:
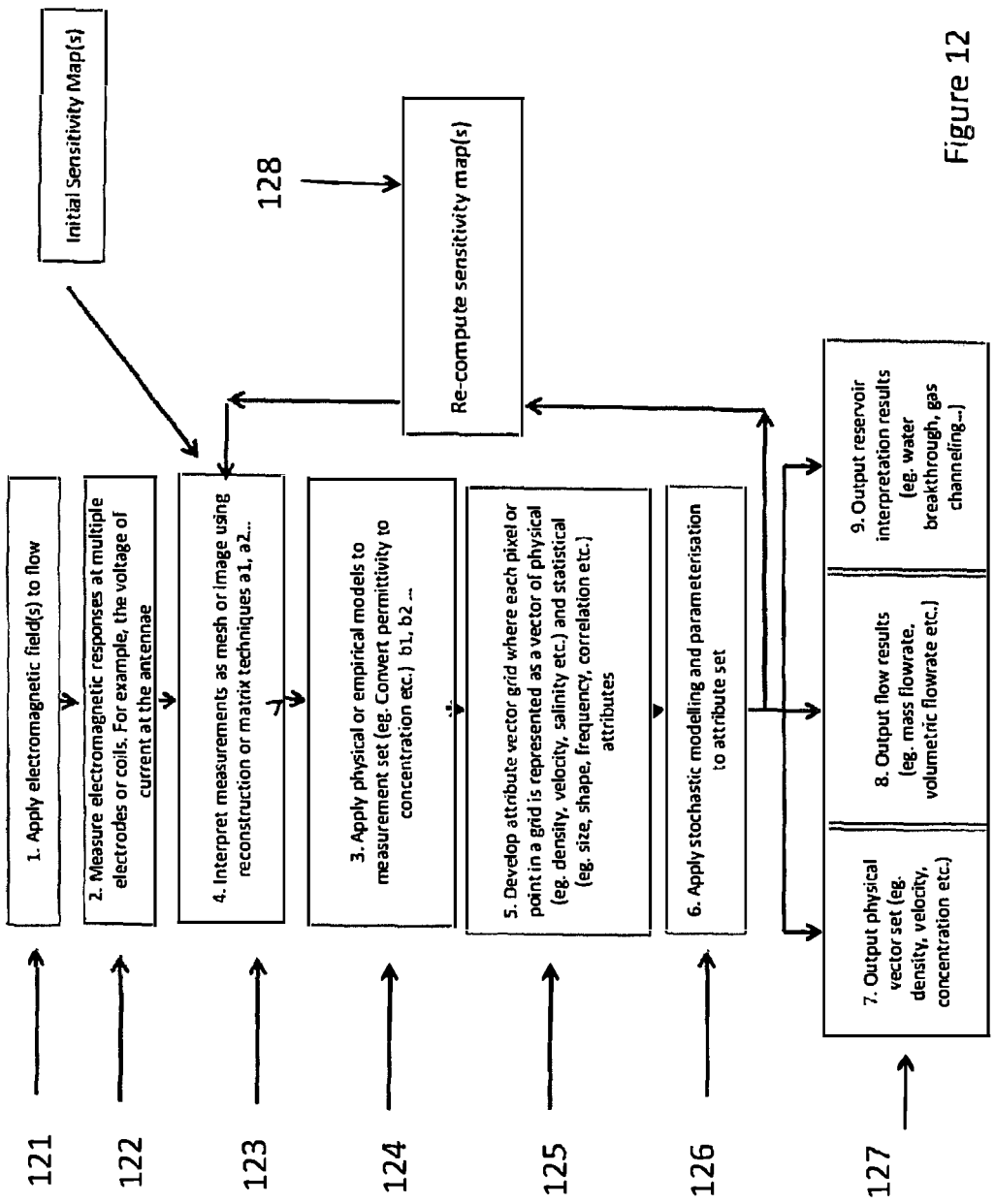
FIG. 12 shows a generalize workflow of processing that creates multiple meshes or images that are in accordance with other embodiments of the present invention.

FIGS. 2a, 2b and 2c illustrate one measurement element, 20, of a device that captures some of the embodiments of this invention. FIG. 2a shows a cross sectional view of the device perpendicular to the direction of flow and FIG. 2b shows a side view along the direction of flow. Referring to FIG. 2a the body of the device allows the multiphase flow, 11 in FIG. 1, to flow through the instrument 20. The channel through the instrument is labelled 10 in all the figures here enclosed. In FIG. 2a the principle or continuous phase in the flow is labelled 12 (e.g. oil) and two additional phases in the flow are labelled 13 (e.g., gas) and 14 (e.g. water). Arranged around the circumference of the pipe 10 are a number of electrodes 26. In this figure there are 8 shown, however, it will be understood by those skilled in the art that this number can be greater or less. The electrodes 26 can be either used to transmit or receive electromagnetic signals. In FIG. 2a electrode 213 is used to transmit an electrical field, which is illustrated as a sine wave, 27. It will be appreciated that this varying signal can be of different forms such as a square wave and these other forms are provided in this invention. The lines of which one is labelled 214, illustrate that the field generated by 213 is transmitted and received by all the other electrodes, 26. It should be noted that the electrodes 26 can be in direct contact with the fluid as shown in FIG. 11 labelled 46 or preferably they are not in direct contact with the fluid flow in 10 as shown in FIG. 10 where an insulating or non-conducting insert, 101, prevents direct contact between the multiphase flow 11 and the electrode 26. This arrangement prevents the build up of water or deposit around the electrodes 26 impacting the performance of the measurement. Clearly such antennae arrangements as shown in FIGS. 11 and 12 are constructed using methods well known in the industry to ensure that there is no leakage of fluid from inside to outside of the pipe 10. It will also be appreciated by those skilled in the art that the field lines 214 emanating from electrode 213 are not straight lines as illustrated in FIG. 2a but more curved equipotential field lines and that FIG. 2a is more a relationship diagram for illustration purposes. The field propagating from 213 is distorted by the different phases, 13 and 14, and the distorted field is pickup at the receiving electrodes. The received signal is illustrated on one electrode and labelled 28. The information content of the measurement can be extracted by combining 27 and 28 in order to obtain the amplitude change and/or phase shift between the transmitted and received signals. The processing of these signals can provide measurements relating to the capacitance and/or resistance contrast between the primary continuous phase and the other phases, 13 and 14, within the flow. This in turn can be used to determine whether the phases are water or oil or gas. At any point in time, one or more electrodes are transmitting and one or more of the others are receiving. The signal can be processed at the receivers either sequentially or in parallel. Once all the received signals have been processed, one or more of the other electrodes becomes the transmitter and again the others are receivers and so forth. As an example, 213, is the first transmitter then the electrode immediately next to it going clockwise becomes the next transmitter. After that the next electrode immediately next to and clockwise to it becomes the transmitter. This continues around all the electrodes and eventually 213 will become the transmitter once more. A second point in the sequencing is illustrated in FIG. 2a where 215 becomes the transmitter and creates an electric field shown as the dashed lines, 216, that are received by the other electrodes. In FIG. 2a it will be appreciated by those skilled in the art that the sequencing can take place in any order and that a complete cycle of measurements, that is, where every electrode has been the transmitter once, can occur very rapidly with, say 500-5000 measurement cycles every second. This rate is only limited by the available processing power, which can be scaled, by known methods, as needed. It will also be appreciated by those skilled in the art that after one complete cycle of measurements a mesh of properties is produced that can be processed to provide a mesh or image of the fluids phases across the section of the pipe. Although this description describes each electrode being either a transmitter or receiver, clearly, a configuration can be provided whereby certain electrodes are always transmitters and others are always receivers. All such combinations are provided in this invention.

Referring to FIG. 2b, it is shown that there are 2 sets of electrodes 26 and 217 that are separated by a known fixed distance 29. Both sets operate in the same fashion and provide independent meshes or images of the flow at two points along the pipe 10. It is possible to cross-correlate the measurements from these two sets, 26 and 217, in order to establish the time-of-flight of features that represent different phases in the multiphase flow 11. This is illustrated in FIG. 2c where 211 shows two curves; one showing a feature passing electrodes 26 and the second the same feature passing electrodes 217. The time difference between the features provides the time it takes for this phase to travel from 26 to 217, that is, the distance 29. Those skilled in the art will appreciate that the velocity of this phase is easily computed from this information. In FIG. 2c, 212 illustrates features that result from a different phase in the flow and in this case the time difference is longer illustrating that this phase is travelling slower that the first phase shown by 211. It will be understood by those skilled in the art that the features shown by 211 and 212 could be derived by cross-correlating the mesh elements at the same location in the cross section of the pipe, such that a velocity profile across the cross section of the pipe is obtained. That is, a mesh or image of velocities is produced that can be used to establish the velocity differences between the primary/continuous phase, phase labelled 13 and the phase labelled 14. It will be appreciated that while FIG. 2a shows 3 phases (12, 13 and 14), it is possible that more can be present and in particular solids (e.g. sand) can also be present. Also, these velocities can be obtained when the primary or continuous phase is either conducting (e.g. water) or non-conducting fluid (e.g. oil).

The electromagnetic measurement, 20, as described above will provide phase concentration measurements where the different phases or constituents are flowing in a predominately non-conducting primary phase 12. If the primary phase is conducting, for example, is mostly water, then this measurement may not provide reliable phase concentration measurements. Therefore, electromagnetic measurement 20, on its own, is insufficient to provide a multiphase flowmeter with a broad range of applications as required for oil and gas measurements. As a result, this invention combines this measurement with others in order to provide a complete solution.

In FIGS. 3a, 3b and 3c is shown a schematic of another measurement element, 30, that captures some embodiments of this invention. FIG. 3a shows a cross-section that is taken perpendicular to the flow and FIG. 3b is a view parallel to the flow. Referring to FIG. 3a there are a plurality of antennae, 36, arranged around the circumference of the instrument. In this measurement these are coils rather than the electrodes used in measurement 20 shown on FIGS. 2a and 2b. Additionally, the antennae shown in FIGS. 3a and 3b can be in direct contact with the multiphase fluid flowing, 12, in the pipe 10, but preferably they are not in direct contact with the fluid and arranged as schematically shown in FIG. 10. In this case, there is non-conducting sleeve, 101, between the antennae 36 and the flow 11. This arrangement prevents the build up of water or deposit around the coils 36 impacting the performance of the measurement. In FIG. 3a the continuous or primary fluid phase or constituent is labelled 12, e.g., oil. Two other phases or constituents are shown diagrammatically as 13 and 14; these could be gas and water, respectively. Each of the antennae 36 can act as either a transmitting or receiving coil and can change between the two modes. In FIG. 3a antennae 313 is shown as a transmitter. A varying electric current is passed through the coil 313 as illustrated by the sign wave 37. Although this varying signal is shown as a sine wave it could be of another form, e.g., square wave and all other potential forms are provided in this invention. The varying electric current passing through the coil 313 will generate a varying magnetic flux through the multiphase fluid 11 that is within the pipe. The magnetic flux lines are schematically shown and one is labelled 314 for illustration purposes. Depending on the physical properties of the different phases that the flux lines interrogate and in particular the conductivity contrast between, e.g., phases 12 and 14, a varying current is induced in the second phase, 14. This is shown schematically and labelled 315 in FIG. 3a. This induced current will in turn generate a secondary varying magnetic field that will propagate through the pipe where it will be pickup by the other antennae that are used as receivers. This secondary varying magnetic field is shown as dashed lines and labelled 316 in FIG. 3a and will induce varying currents in the receiver coils. This is shown schematically in one coil on FIG. 3a and labelled 38. Comparing 37 and 38 with appropriate processing, for example, the phase shift between the signals, allows the conductivity contrast between the materials, for example, 12, 13 and 14, to be computed.

In a similar fashion described for measurement 20 earlier, at any point in time there is one coil that is transmitting and all of the others are receiving. Once all the receiver coils signals have been processed, one or more of the other coils becomes the transmitter and again the remainder are receivers and so forth. As an example, 313 is the first transmitter coil then the coil immediately next to it going clockwise becomes the next transmitter. After that, the next coil immediately next to and clockwise to it becomes the transmitter. This continues around all the coils and eventually 313 will become the transmitter coil once more. In FIG. 3a it will be appreciated by those skilled in the art that the sequencing can take place in any order and that a complete cycle of measurements, that is, where every coil has been the transmitter once, can occur very rapidly with, e.g., 500 to 5000 measurement cycles every second. This frequency being primarily limited only by the processing power available that can be scaled as needed. It will also be appreciated by those skilled in the art that after one complete cycle of measurements a mesh of properties is produced that can be processed to provide a mesh or image of the fluids phases across the section of the pipe. Although this description describes each coil being either a transmitter or receiver, clearly, a configuration can be provided whereby certain coils are always transmitters and others are always receivers. In other embodiments coils can be enclosed within other coils so that dedicated transmitter and receiver coils are at the same location. Those skilled in the art will appreciate that many combinations are possible and all such combinations are provided in this invention.

Referring to FIG. 3b, it is shown that there are 2 sets of coils 36 and 317 that are separated by a known fixed distance 39. Both sets operate in the same fashion and provide independent meshes or images of the flow at two points along the pipe 10. It is possible to cross correlate the measurements from these two sets, 36 and 317, in order to establish the time-of-flight of features that represent different phases in the multiphase flow 11. This is illustrated in FIG. 3c where 311 shows two curves; one showing a feature passing coils 36 and the second the same feature passing electrodes 317. The time difference between the features provides the time it takes for this phase to travel from 36 to 317, that is, the distance 39. Those skilled in the art will appreciate that the velocity of this phase is easily computed from this information. In FIG. 3c, 312 illustrates features that result from a different phase in the flow and in this case the time difference is longer illustrating that this phase is travelling slower than the first phase shown by 311. It will be understood by those skilled in the art that the features shown by 311 and 312 could in fact be derived by cross correlating the mesh elements at the same location in the cross section of the pipe such that a velocity profile across the cross section of the pipe is obtained. That is, a mesh or image of velocities is produced that can be used to establish the velocity differences between the primary/continuous phase, phase labelled 13 and the phase labelled 14. It will be appreciated that while FIG. 3a shows 3 phases (12, 13 and 14); it is possible that more can be present and in particular solids (e.g. sand) can also be present. Also, these velocities can be obtained when the primary or continuous phase is either conducting (e.g. water) or non-conducting fluid (e.g. oil).

The electromagnetic measurement, 30, as described above will provide measurements where there is a conductivity contrast between the phases. This is possible when the different phases or constituents are flowing in a predominately conducting (e.g. water) or non-conducting (e.g. oil) primary phase 12. However, where there is a very small difference in the conductive between phases, e.g., between oil and gas, then measurement may not provide reliable results. Therefore, 30 on its own, is not sufficient to provide a multiphase flowmeter with a broad range of measurement as required for oil and gas applications. As a result, this invention combines this measurement with others in order to provide a complete solution.

Figure 4A:
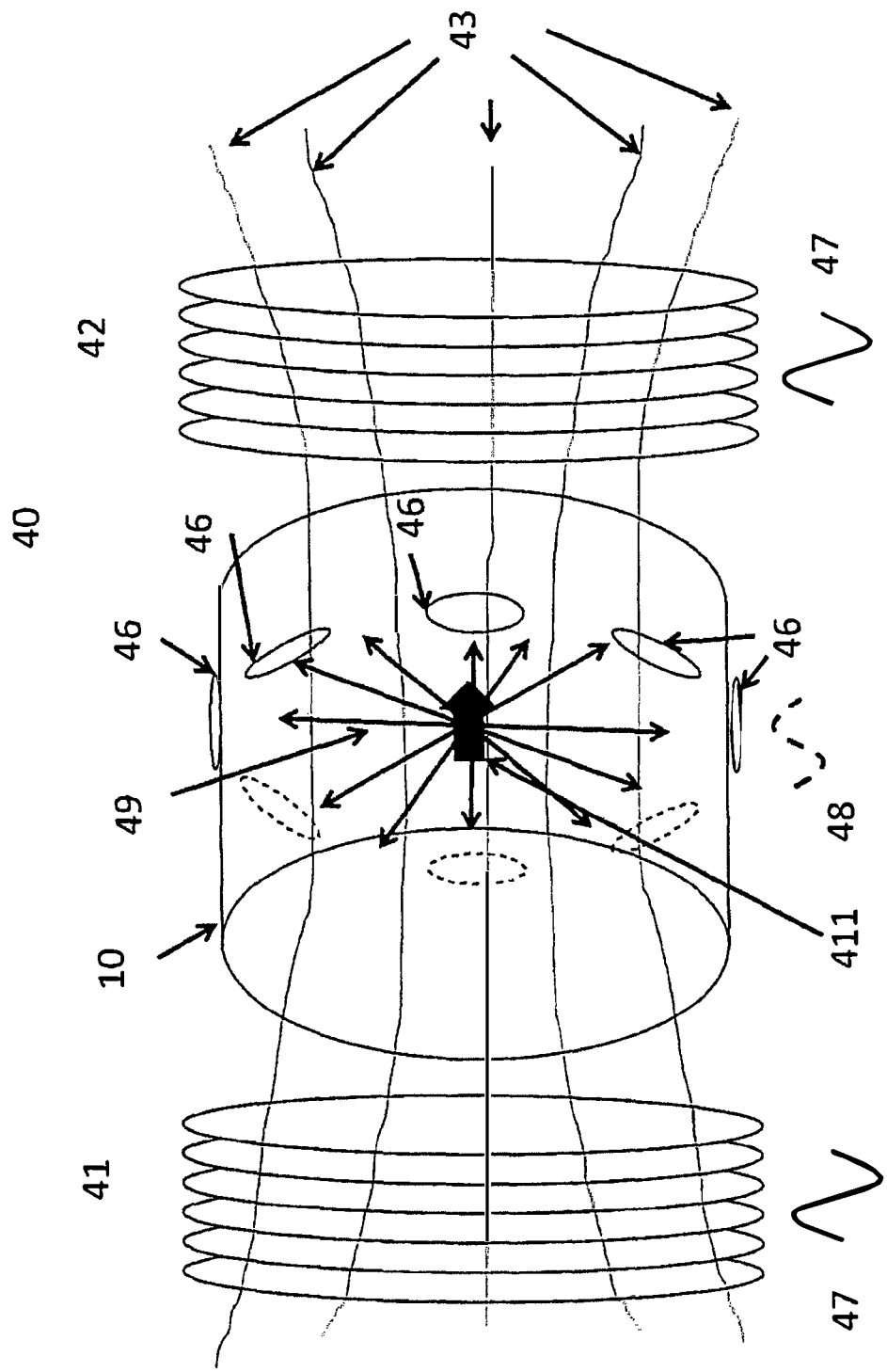
FIGS. 4a, 4b and 4c illustrate yet another electromagnetic measurement that is in accordance with yet another embodiment of the present invention.
Figure 4B:
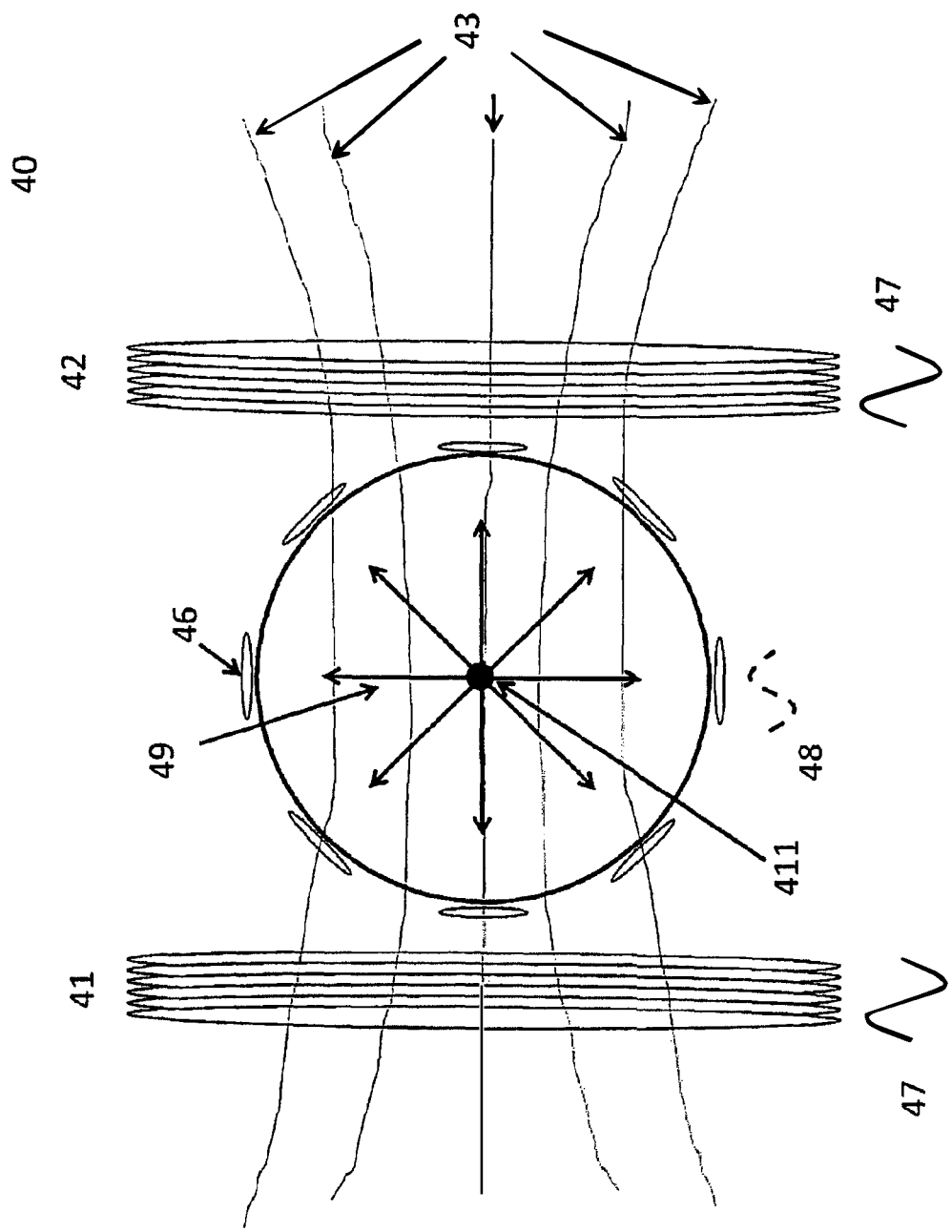
Figure 4C:
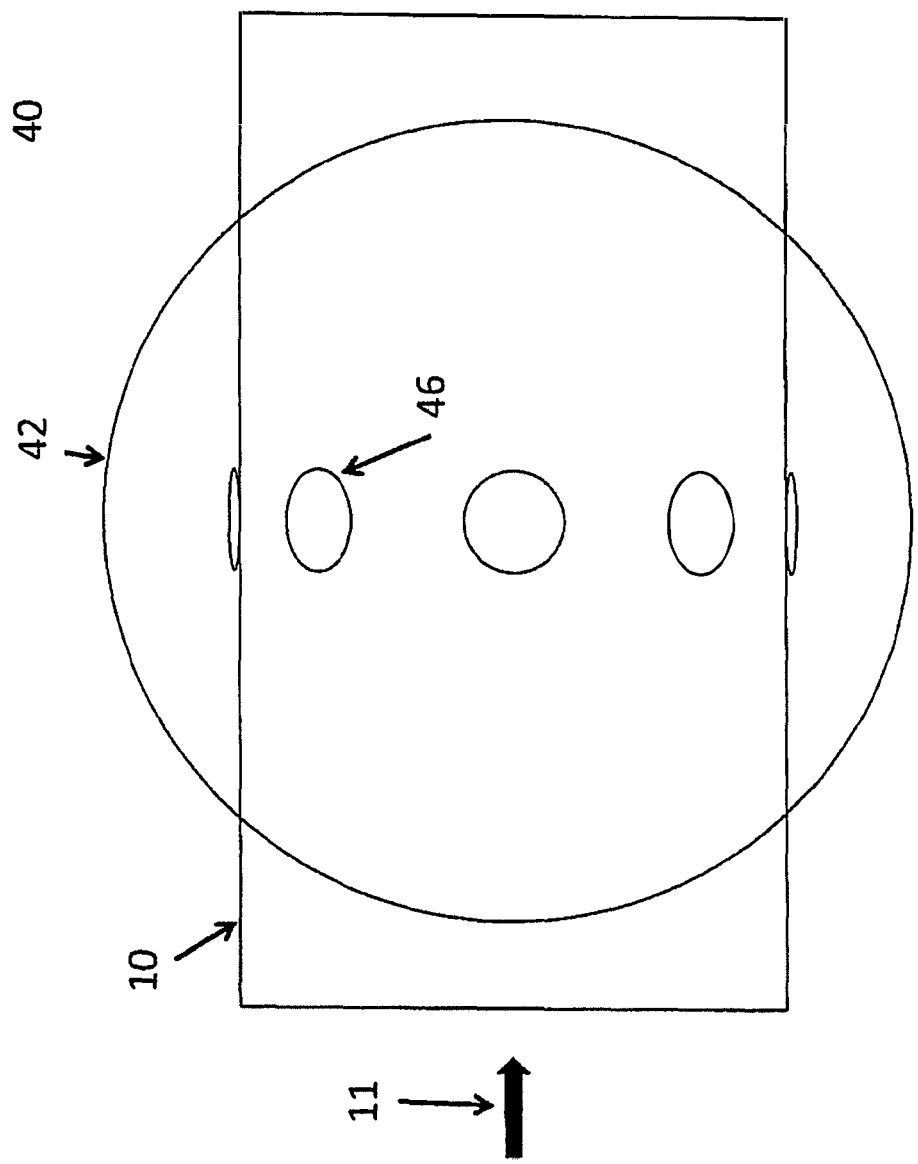

FIGS. 4a, 4b and 4c described yet another measurement element, 40, that captures some embodiments of the present invention. FIG. 4a, illustrates a 3D perspective view, FIG. 4b shows a cross section view perpendicular to the flow and FIG. 4c shows a side view. Referring to FIG. 4a there is shown a pipe 10 with a multiphase flow passing through it and labelled 411. Either side of the pipe 10 of the measurement element 40 there are 2 coils labelled 41 and 42 in FIGS. 4a, 4b and 4c. Additionally and arranged around the circumference of the pipe 10 are antennae shown as electrodes 46. These electrodes can be electrically insulated from the multiphase flow fluid 411 in the pipe as illustrated in FIG. 10 or preferably they can be in electrical contact with the fluid as shown in FIG. 11. In FIG. 11 there is a non-conducting sleeve 111, which has the 46 electrodes disposed on it. The electrodes 46 are flush with the internal surface of 111 such that they do not interfere with the flow passing through the pipe 10 but they are in electrical contact with this fluid.

Referring to 4a and 4b, there is shown that a varying electric current is applied to the coils 41 and 42 and schematically illustrated 47 in both figures. It will be appreciated by those skilled in the art that these varying currents although shown as sine waves, could be of another form, for example, square waves. The currents in these coils will generate magnetic flux lines that pass through the pipe 10 and are illustrated on both figures and labelled 43. It will be appreciated that pipe 10 needs to be constructed of appropriate materials to allow the propagation of flux lines 43 with minimal interference and those skilled in the art will understand that this can be achieve by several means including using a section of pipe that is non-conducting. In FIGS. 4a and 4b the multiphase flow 411 passing through the pipe has a primary or continuous phase that is conducting (e.g., water). As this conducting fluid traverses or cuts through the flux lines 43 a voltage is generated as illustrated by the lines labelled 49. This voltage will be varying with the field and proportional to the velocity of the conducting phase. Additionally, this varying voltage is received on the electrodes, 46, and is illustrated on one electrode as a varying signal 48. It will be understood by those skilled in the art that the application of appropriate processing to the received signals on all electrodes 46 can produce a mesh or image of the velocity profile of the said conducting phase across the cross section of the pipe 10.

The electromagnetic measurement, 40, as described above will provide the velocity profile measurements where the different phases or constituents are flowing in a predominately conducting primary phase 12. If the primary phase is non-conducting, for example, is mostly oil, this measurement may not provide reliable velocity measurements. Therefore, electromagnetic measurement 40, on its own, is not sufficient to provide a multiphase flowmeter with a broad range of measurement as required for oil and gas applications. As a result, this invention combines this measurement with others and appropriate processing in order to provide a complete solution.

The following FIGS. 5 through 9 provide illustrations of several preferred embodiments of this invention and each will now be described.

Figure 5:
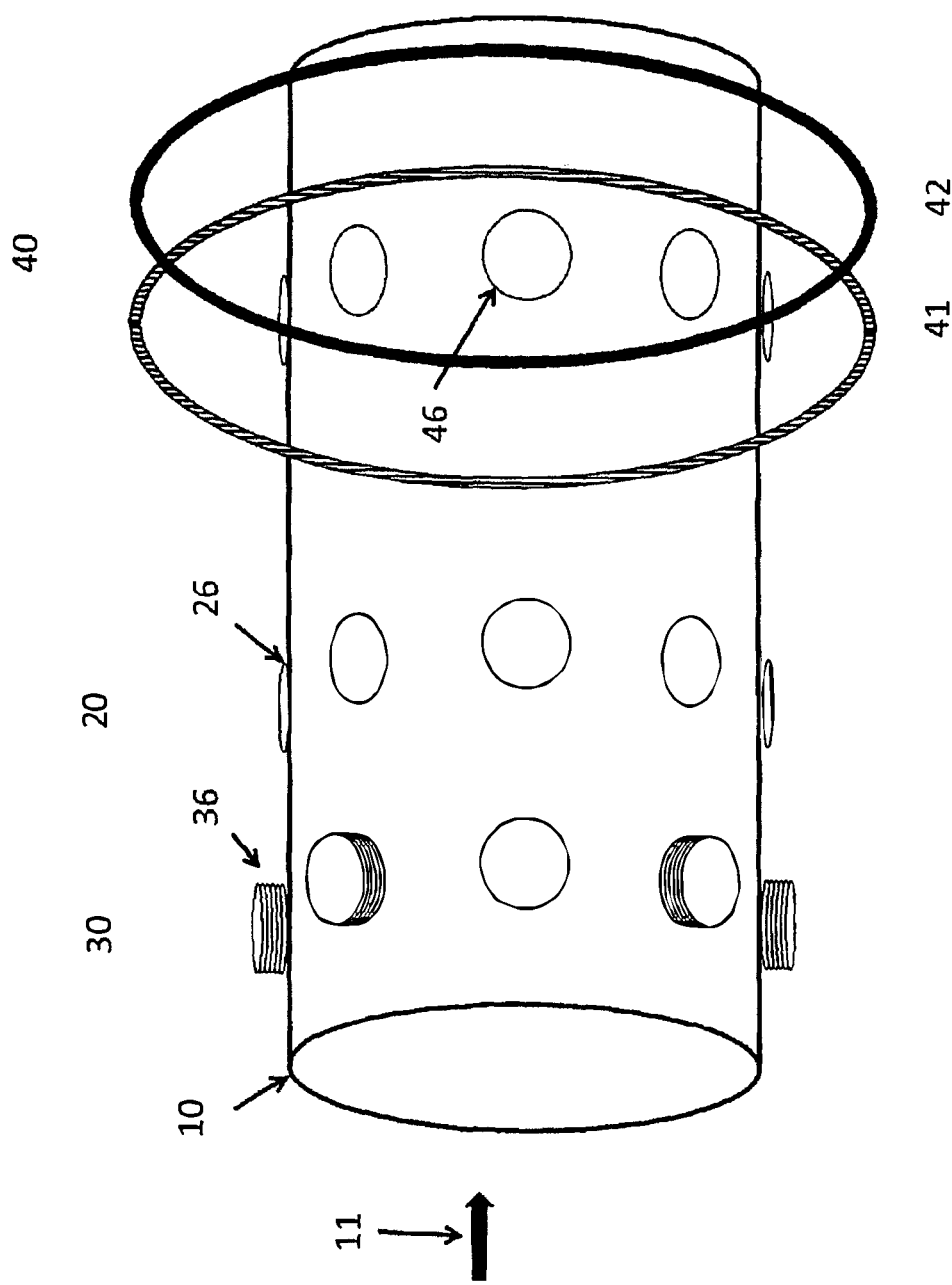
FIG. 5 illustrates a device configuration that combines electromagnetic measurements that is in accordance of yet another embodiment of the present invention.

Referring to FIG. 5 there is shown a multiphase flow 11 flowing through a pipe 10 that can be the main body of the multiphase flow meter. FIG. 5 shows a schematic of a multiphase flowmeter that represent one embodiment of this invention. The meter shown in FIG. 5 comprises three measurements 20, 30 and 40 as described individually earlier in this document. Each measurement provides information independent of the others. Additionally, each measurement provides a mesh or image of measurements that are physically complimentary in producing a continuous and real-time mesh or image of all the different phases or constituent components of the multiphase flow 11. This will be described in detail in a later section of this document. In FIG. 5 from left to right is shown the measurement 30 with its antennae coils 36 arranged around the circumference of the pipe 10 as described earlier. To the right of this is shown the measurement 20 with its antennae labelled as 26. Finally on the right hand side of the pipe 10 is shown the measurement 40 with its two larger coils 41 and 42 placed on either side of the pipe 10 and its receiver antennae 46 arranged around the circumference of the pipe 10. It will be appreciated by those skilled in the art that this is just one of many arrangements and these measurements could in fact be in any order going from one side of the instrument illustrated in FIG. 5 to the other side and all other combinations are provided in this invention.

Figure 6:
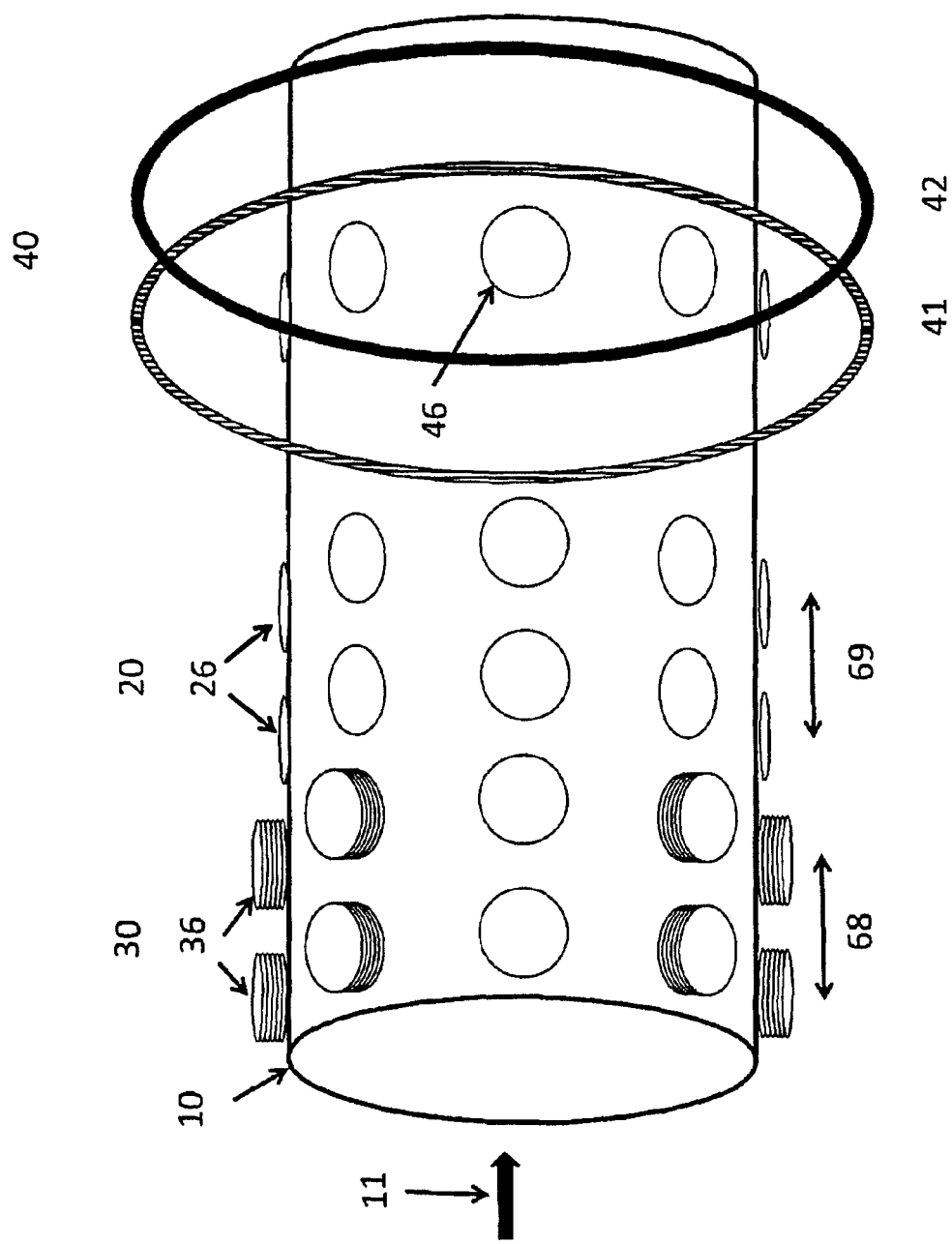
FIG. 6 shows a schematic of yet another configuration of a device combining several electromagnetic measurements that is in accordance of a further embodiment of the present invention.

Referring to FIG. 6, which shows a schematic of a multiphase flowmeter that represents another embodiment of this invention. In FIG. 6 a multiphase flow, 11, is shown flowing through a pipe 10 that can be the main body of the multiphase flow meter. In this embodiment the multiphase flowmeter comprises three measurements 20, 30 and 40 as described earlier. This is similar to the embodiment shown in FIG. 5, however, in FIG. 6 there is illustrated two sets of antennae 36 and 26, each set separated by a known distance 68 and 69, respectively. That is, measurements 20 and 30 are repeated along the axis of the pipe. As a result, cross correlations of the measurements made by the sets of antennae for measurements 30 and 20 can be processed as described earlier to provide meshes or images of the velocity profiles of the different phases or constituent components of the multiphase flow 11. The pairs of measurements for 20 and 30 are quite independent of each other providing unique data sets. It will also be appreciated by those skill in the art that while two sets of antennae for measurements 20 and 30 are shown and only one set of antennae for measurement 40 is shown, there could in fact be more (or less) sets utilized for each measurement and that all other combinations are provided in this invention.

Figure 7:
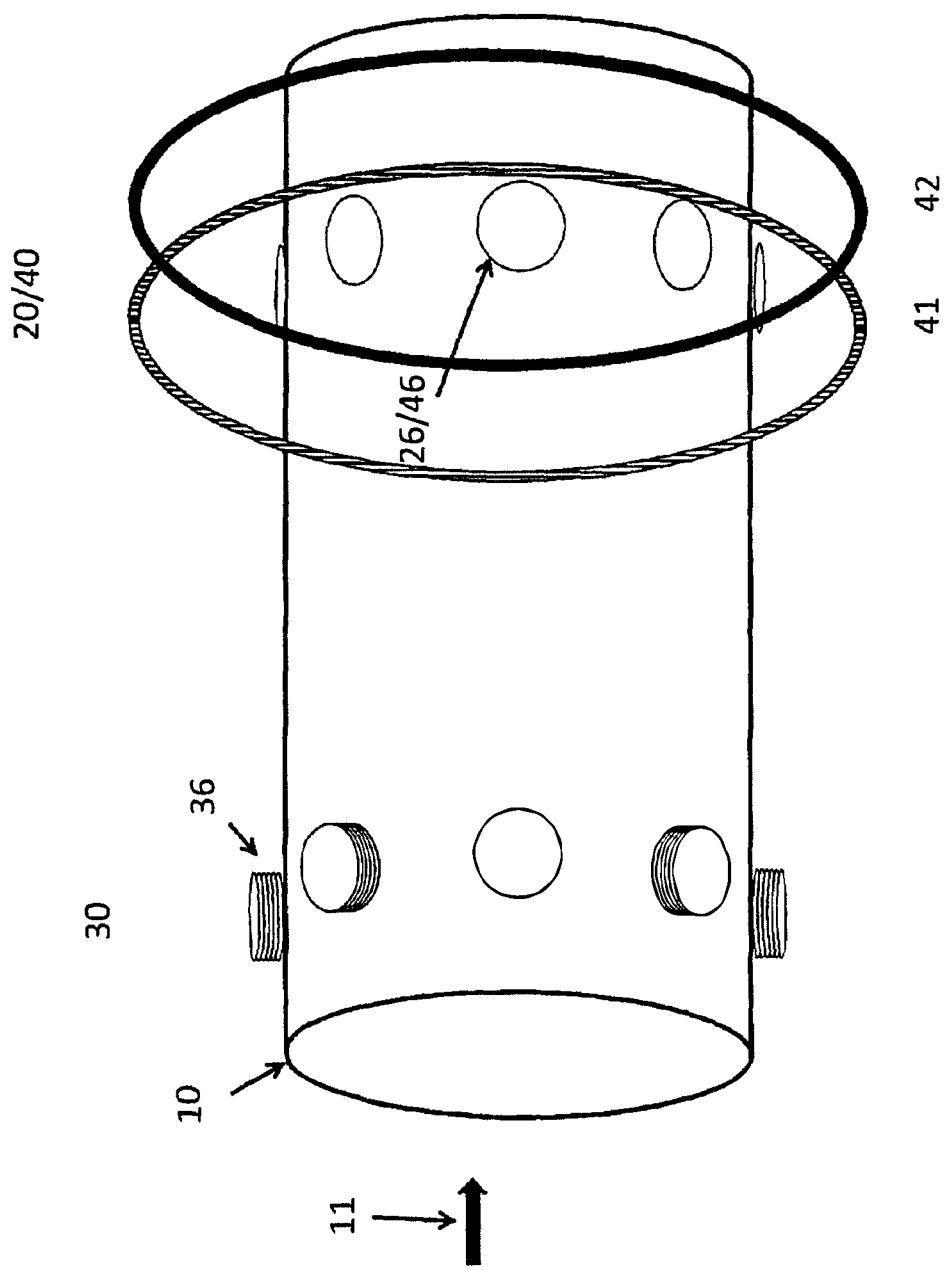
FIG. 7 illustrates yet another device configuration that is in accordance of another embodiment of the present invention.

FIG. 7 illustrates yet another embodiment of this invention. In FIG. 7 measurements 20 and 40 share the same antennae. In this case, it will be appreciated by those skilled in the art that the larger coils 41 and 42 can remain inactive while the antennae labelled 26/46 is used as described above to make the measurement 20. The coils 41 and 42 can then be made active so that the antennae labelled 26/46 can be used to perform the measurement 40 as described earlier. The antennae coils labelled 36 in FIG. 7 can be used to provide the independent measurement, 30, as described earlier. In this way the size of the final multiphase flowmeters can be reduced while maintaining the number of measurements. It is also provided in this embodiment that multiple sets of antennae 36 and 26/46 can be utilized in this configuration to provide additional measurements for cross correlation purposes as described earlier.

Figure 8:
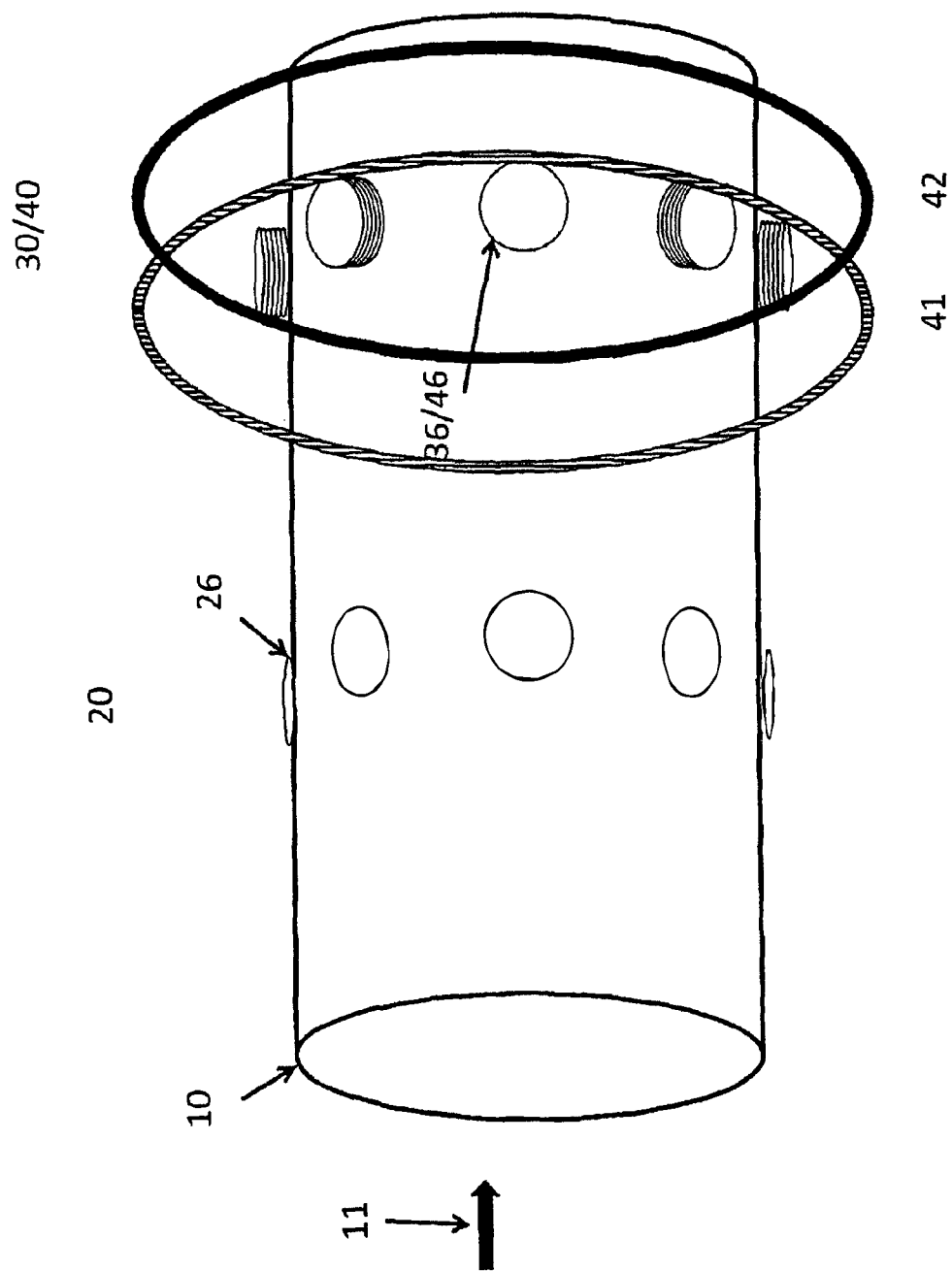
FIG. 8 shows a further device that is in accordance with another embodiment of the present invention.

FIG. 8 illustrates yet another embodiment of this invention. In this configuration measurements 30 and 40 share the same antennae labelled 36/46. In this case, the coils 41 and 42 can be alternatively active and inactive so that the measurement 30 and 40 can be made sequentially. The measurement, 20, as described earlier is made using antennae 26 in FIG. 8. In this way the size of the final multiphase flowmeters can be reduced without the loss of the number of measurements. It is also provided in this embodiment that multiple sets of antennae 26 and 36/46 can be utilized in this configuration to provide additional measurements for cross correlation purposes as described earlier.

Figure 9:
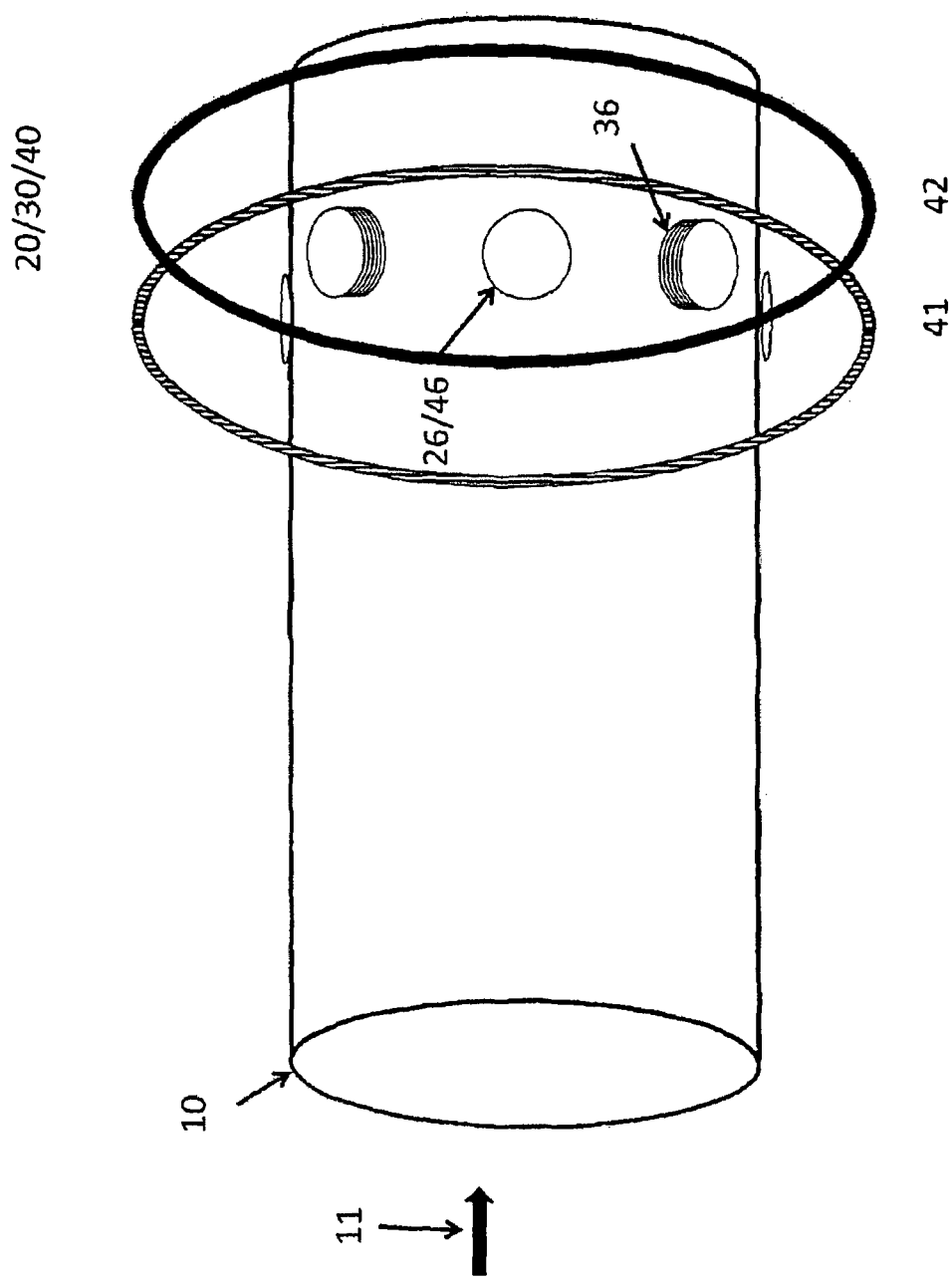
FIG. 9 illustrates another device configuration that is in accordance of yet a further embodiment of this invention.

Referring to FIG. 9 yet another embodiment of this invention is shown. In FIG. 9 all three measurements 20/30/40 are combined to share the same antennae labelled 26/46 and 36. It will be appreciated by those skilled in the art that the antennae in this configuration will comprise both electrodes as labelled 26/46 and coils as labelled 36 in FIG. 9. The coils 41 and 42 can be made to be inactive while the measurements 20 and 30 are being made. They can then be made active so that measurement 40 can be made. It will be appreciated that by using different signal frequencies generated by 41/42 and antennae coils 36 it is possible to make the measurements 30 and 40, concurrently and with measurement 20. In this case, the multiphase flowmeter can be made shorter. It is also provided in this embodiment that multiple sets of antennae 36 and 26/46 can be utilized in this configuration to provide additional measurements for cross correlation purposes as described earlier.

Those skilled in the art will appreciate that what is described in FIGS. 1-12 is a limited set of examples which clearly defines the concept captured in this invention and that many different embodiments of this invention are possible. These other embodiments are provided as part of this invention.

FIGS. 1 through 11 describe instrumentation that represents embodiments of the present invention. However, in order to extract the multiphase flow parameters from the measurements captured using these instruments, it is necessary to provide signal processing and algorithms to process information captured in the meshes or images. This will now be described using FIGS. 12 through 16. Referring to FIG. 12 there is shown a generalized flow chart that captures the steps describing an embodiment of this invention. In FIG. 12 the first step, 121, shows that electromagnetic field or fields are applied to the multiphase flow. As described earlier, there can be many different types of electromagnetic fields. In the step 122, it is shown that the electromagnetic response at multiple electrodes or coils is captured and several embodiments of the equipment used for this purpose shown earlier in this disclosure.

Figure 13:
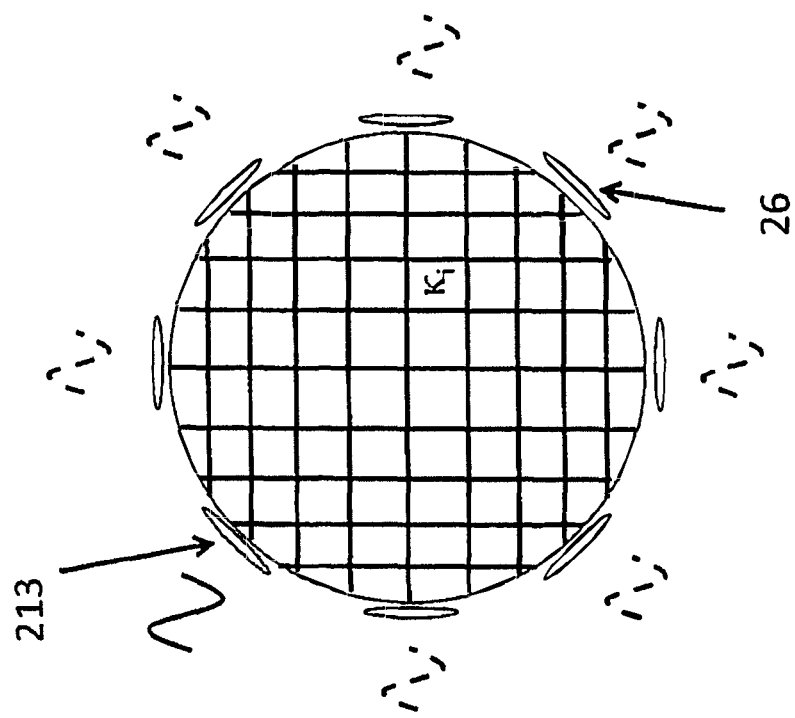
FIG. 13 shows a method of calculating a sensitivity matrix necessary for some embodiments of the invention.

The measurements of electromagnetic response acquired at step 122 may be interpreted as responses to a distribution of materials across the pipe with different physical properties. FIG. 13 illustrates this concept: when a material of electrical permittivity Ki is conceptually placed at grid location i, the use of electrode 213 as transmitter leads for example to response at electrode 26 which is a function of the value and location of Ki. These responses may be presented as a grid or matrix, commonly known as a sensitivity map. It is to be understood that a sensitivity map of this type may be used to relate the distribution of physical parameters such as permittivity, conductivity, salinity or velocity to voltage, current or other electromagnetic properties.

The electrical measurements, physical material properties and derived quantities may be called attributes of the flow, and each location in the grid or mesh across the pipe will have many such attributes associated with it. This is shown in FIG. 14 where 141 represents the mesh of parameters and 142 labels the attribute lists at each element of the mesh. In FIG. 14 the attribute lists 142 &144 contains both measurements, listed a1, a2, a3 etc., and processed attributes; b1, b2, b3 . . . and c1, c2, c3 . . . etc. However, it will be understood by those skilled in the art that the meshes and attribute lists could be split into those that contain raw measurements and those that contain processed values or some other combination.

Returning to FIG. 12, 124 labels the step in the flow chart where physical or empirical models are applied to the electromagnetic measurements to compute parameters that represent the multiphase flow. For example, convert capacitance into concentration of a particular phase or constituent component (e.g., oil, water or gas) or convert voltage into salinity. This step can involve multiple models mapping a measurement or several measurements, including cross-correlations as described earlier in this disclosure. It is also understood by those skilled in the art that multiple values of attributes can result in this step, for example, when examining FIG. 2a, it can be seen that when electrode 213 is the transmitter and 215 is the receiver measurements are made along the path between the two electrodes and this will be repeated when 215 is the transmitter and 213 is the receiver. That is, multiple measurements can be achieved for the same parameter between 213 and 215. These measures could be averaged to produce single values at each mesh point or they could be treated independently. Other scenarios can exist where different models could be used to produce multiple values of a particular parameter at each mesh point. In step 124 of FIG. 12 such measurements are interpreted and combined using reconstruction or matrix techniques. In 125 a mesh or grid of attribute vectors is created where each pixel of the grid contains a vector. In addition the vector or attribute list is represented as a vector of physical (e.g., density (oil, water or gas), velocity (oil, water or gas), water salinity etc.) and statistical (e.g., size, shape, frequency, probability etc.) attributes.

One embodiment of the present invention takes the mesh of attribute vectors from step 125 and develops relationships between them that may be based on physical models or understanding, or may simply be statistical relationships. These relationships are used to derive a likely distribution of material properties across the pipe. This distribution of material properties is considered to be part of the mesh of attribute vectors and may affect the sensitivity matrix previously calculated before step 123. After step 126 the sensitivity matrix can be recalculated based on the estimated distribution of material properties. Such calculations may be undertaken using mathematical techniques well known in the art, for example by finite element modelling or by the use of analytical mathematical relationships.

Having recalculated the appropriate sensitivity maps step 123 is repeated to develop another estimate of the distribution of material properties. When the difference between one step and the previous is considered sufficiently small the process moves to step 127.

In step 127 the mesh or grid of attribute vectors is integrated or operated on by other physical models to produce estimates of physical properties across the pipe (box 7), and results in time related to the flow of materials (box 8). The outputs calculated in box 8 of step 127 are those traditionally known in flow metering as flow rate, either in mass or volume and it is understood that there will be outputs from box 7 and 8 which describe the density, concentration, velocity and flow rate of each of the material components present in the flow.

In addition to calculation of conventional flow rate information the attribute vectors are used to derive information of direct importance to the physical phenomena occurring in the reservoir from which the fluids are flowing. This is illustrated in box 9.

Figure 15:
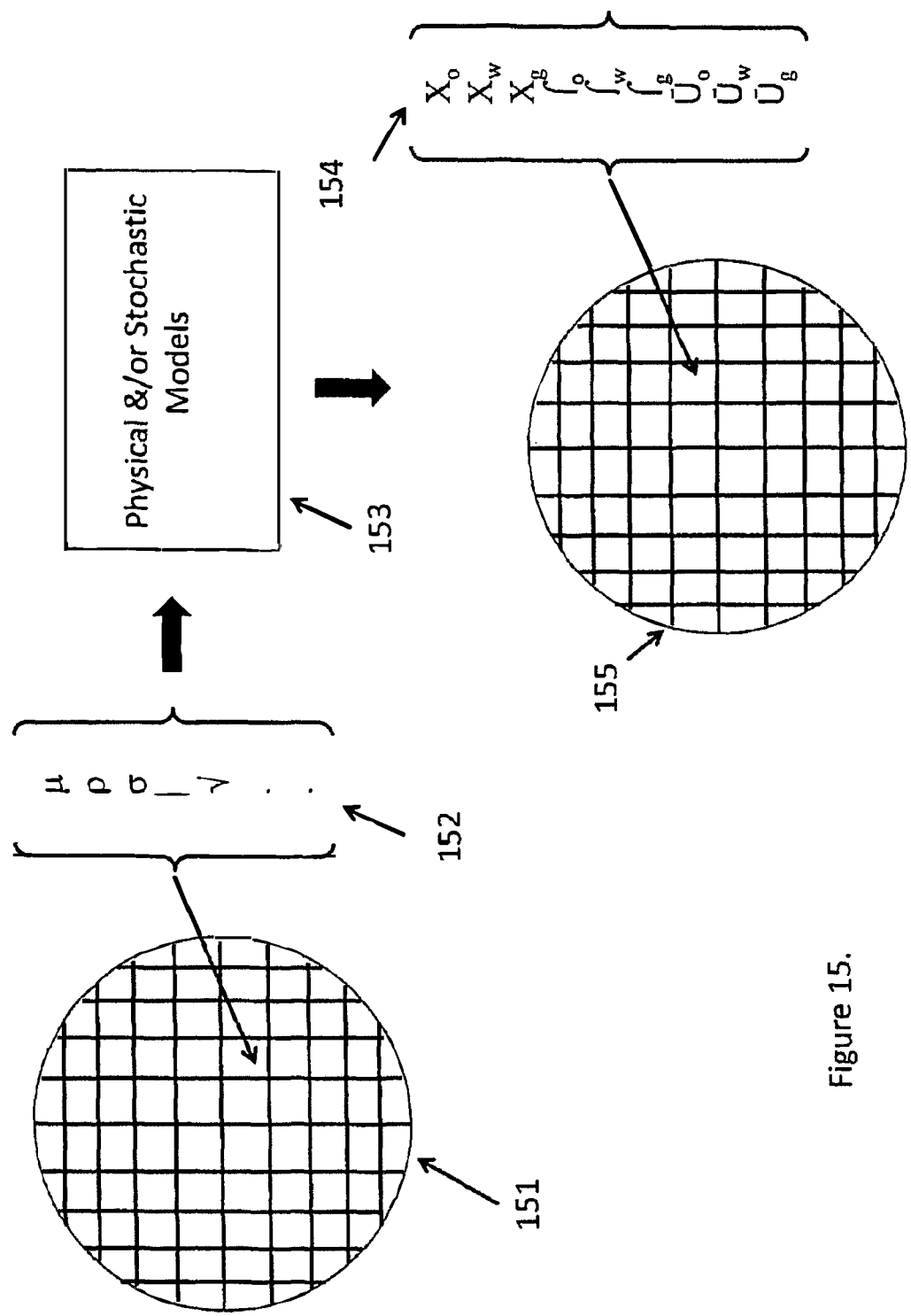
FIG. 15 shows how physical and stochastic models can be used to calculate derived state vectors at each point in a mesh or grid.

FIG. 15 provides another generalized workflow where the cross section of the pipe is represented as a mesh or grid, 151. At each grid point there is an attribute matrix 152 that contains electromagnetic measurements obtained by a range of electromagnetic measurements as previously described, for example, permittivity, conductivity, etc. The mesh or grid 151 is processed using physical and/or stochastic models, 153. The result of such processing is another mesh or grid 155 that has another attribute matrix at each element 154. The attribute matrix 154 has the computed phase concentrations (oil: $X_o$, water: $X_w$ and gas: $X_g$), densities (oil: $\sigma_o$, water: $\sigma_w$ and gas: $\sigma_g$) and velocities (oil: $\overline{U}_o$, water: $\overline{U}_w$, and gas: $\overline{U}_g$).

A typical embodiment of the present invention is a combination of the embodiments of FIGS. 2, 3 and 4 as shown in FIG. 6, together with the processes described in FIG. 12. The electrodes 26 shown in FIGS. 2a, 2b and 2c are used to apply an electric field to the pipe and the resulting vector of measurements of voltage are interpreted as being dependent on the electrical permittivity distribution in the flow. Simultaneously the coils 36 shown in FIGS. 3a, 3b and 3c are used to measure a set of voltages dependent on the conductivity distribution in the pipe, and the magnets/coils 41 and 42 together with electrodes 46 shown in FIGS. 4a, 4b and 4c are used to measure a set of voltages related to the velocity distribution of the continuous phase. These measurements may be considered to be those shown in steps 121 and 122 of FIG. 12. Three sensitivity maps are calculated: (1) to relate voltage measured at antennae 26 to permittivity at each point in the mesh 141 (FIG. 14), (2) relating phase angle measured at coils 36 to conductivity at each point in the mesh 141 (FIG. 14) and (3) to relate voltage measured to continuous phase velocity at each point in the mesh 141 (FIG. 14). The process starts with initial sensitivity maps that can be recomputed in an iterative fashion described later. The three sensitivity maps are combined with the related measured voltages and phase angles to estimate the values of permittivity, conductivity and continuous-phase velocity at each point in the mesh 141. These values may be considered as equivalent to the attributes shown in vector 144 in FIG. 14 as b1, b2 and b3.

A second mesh of attribute vectors is created in the same way for the measurements in the second plane or set, of antennae 36 and 26, shown in FIG. 6. The attributes a1 and a2 are recorded against time approximately 500 to 5000 times per second and mathematically cross-correlated with the time series of their respective attributes in the first vector. The resulting calculated time delays are divided by the distance between the antennae; 68 and 69, to estimate velocities. At this stage the velocities are not allocated to a particular phase but are allocated to the attribute vector of the first plane as, for example, c1 and c2 as shown in vector 145 of FIG. 14.

Figure 16:
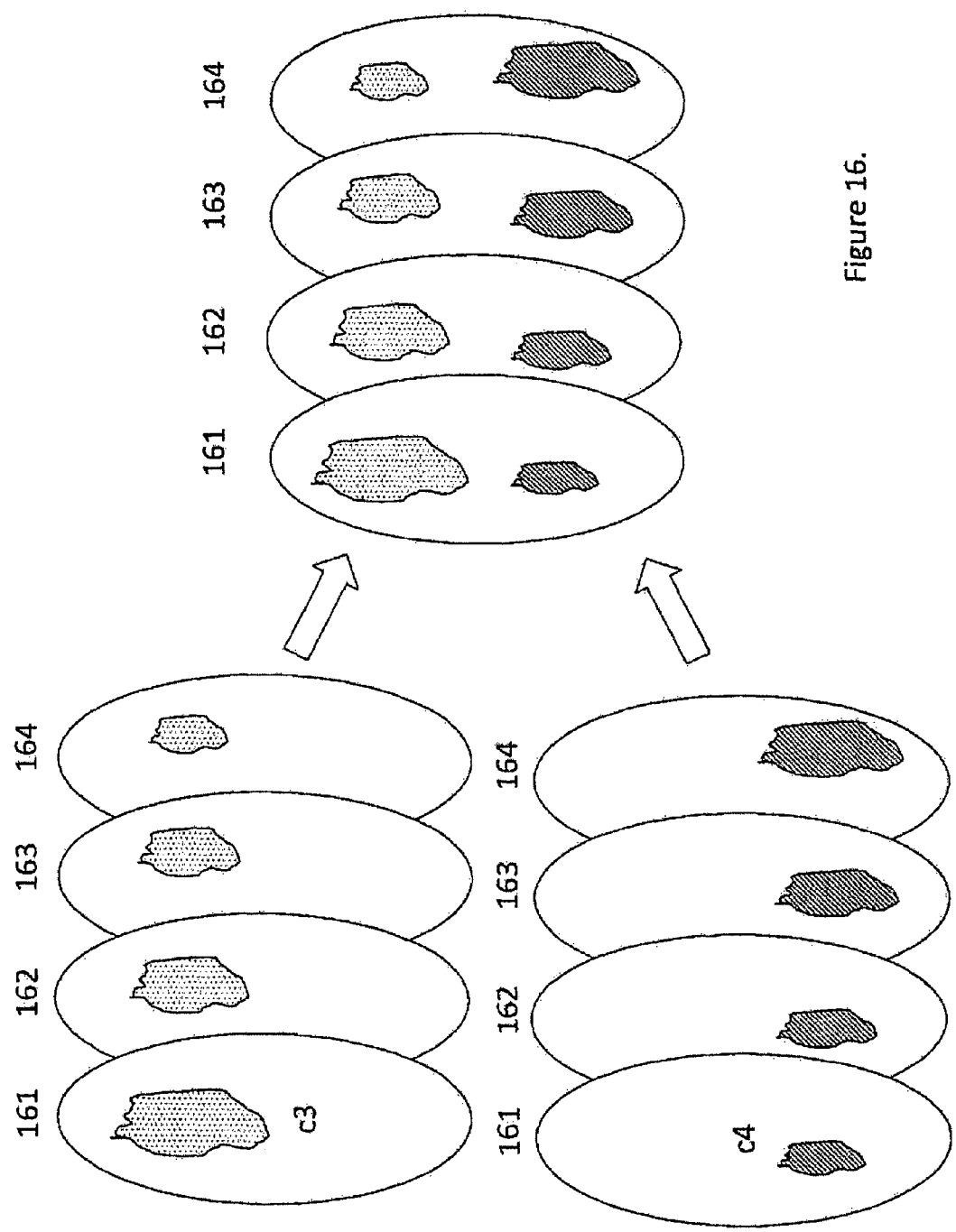
FIG. 16 shows how two different images derived from different measurements may be integrated to a single combined image.

Physical models linking electrical measurements to concentration are now used in step 124 of FIG. 12 to convert permittivity and conductivity into estimates of concentration. Such calculations may use for example equations previously published in Hunt 2012. The resulting values of concentration may be mapped as meshes or images of data as indicated diagrammatically in FIG. 16 where estimates of c3 and c4 from the attribute vectors are combined spatially to give an indication of shape and size of different phases or clusters of phases. In FIG. 16 measurements are taken at a regular time interval and images labels 161, 162, 163 and 164 illustrate the data capture at each time step. Clearly such images can be used to produce a movie. For example, it can be seen in the combined images on the right hand side for FIG. 16 that the c3 attribute is shrinking with time while the c4 attribute is getting large with time. Integration of the area each attribute, for example, c3, as a function of time provides a volume rate of this particular attribute. Those skilled in the art will appreciate that imaging processing techniques can be applied to such images to compute various features including surface areas, volume rate and mathematical values representing the spacial distribution.

Vector 145 in FIG. 14 is now used as step 125 in FIG. 12 and physical and/or stochastic models are used to link the different parameters in step 126. For example attributes b1 representing low permittivity values if associated with high values of velocity 26 (In vector 145 the numbers 26, 36 and 46 are used to signify the antennae that have been used to determine the respective parameters) are considered to be part of gas structures, such gas bubbles typically moving faster than the average flow. Attributes b1 representing low permittivity values if associated with low values of velocity 26 are considered to be part of oil structures, such oil bubbles typically moving slower than gas bubbles but faster than the continuous velocity b3. Attributes b2 representing high conductivity values if associated with low values of velocity 26 are considered to be part of water structures, such water bubbles typically moving slower than the average flow. It is understood that these relationships are only examples of those that may be used in the present invention, many others being possible and are provided in this invention.

Each point in time at each position in the mesh of measurements can now be allocated to a particular phase, and the density of that phase is estimated using physical or statistical models or samples from elsewhere in the process.

After step 126 the sensitivity matrix can be recalculated based on the estimated distribution of material properties. Such calculations may be undertaken using mathematical techniques well known in the art, for example by finite element modelling or by the use of analytical mathematical relationships.

Having recalculated the appropriate sensitivity maps in step 128, step 123 is repeated to develop another estimate of the distribution of material properties. When the difference between one step and the previous is considered sufficiently small the process moves to step 127.

In this way the attribute vector which may contain 10 to 50 variables or more, starts on the first iteration as a first guess and the re-computing 128 of the set of sensitivity maps at each iteration makes that guess closer to the final estimate. The iteration may be repeated at each point in time, and the starting point for the next point in time may be the finishing point of the previous point in time, since in general the velocities, concentrations and phases will change very much more slowly than the rate of data acquisition.

In step 127 the mesh or grid of attribute vectors is integrated or operated on by other physical models to produce estimates of physical properties across the pipe (box 7), and results in time related to the flow of materials (box 8). The outputs calculated in box 8 of step 127 are those traditionally known in flow metering as flow rate, either in mass or volume and it is understood that there will be outputs from box 7 and 8 which describe the density, concentration, velocity and flow rate of each of the material components present in the flow.

Figure 17B:
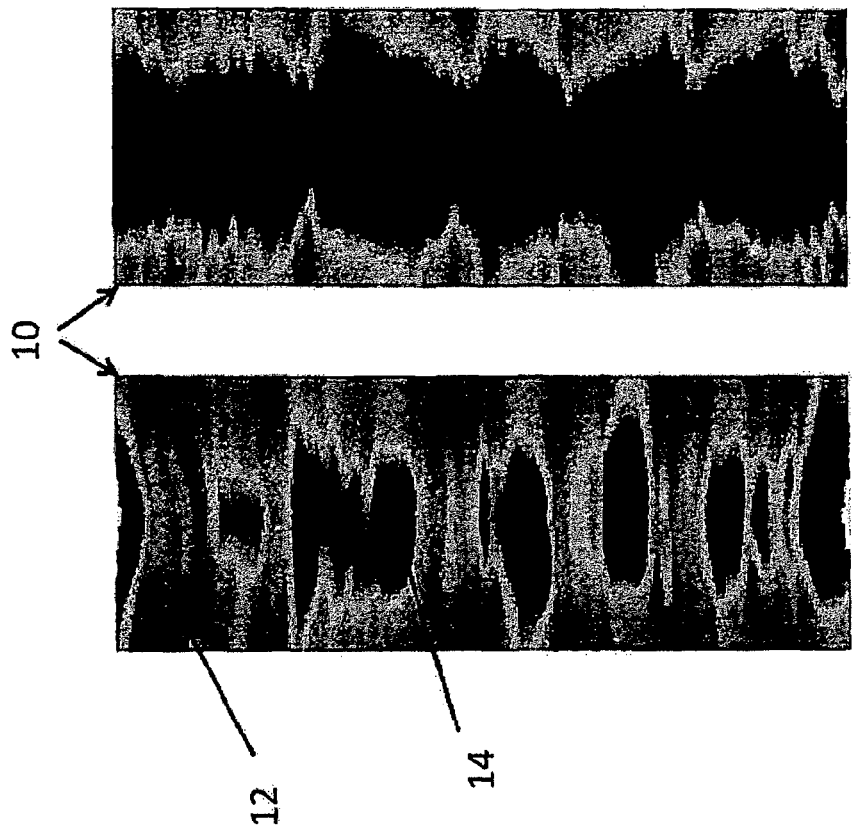
FIGS. 17a and 17b show output images that are in accordance with embodiments of the present invention.
Figure 17A:
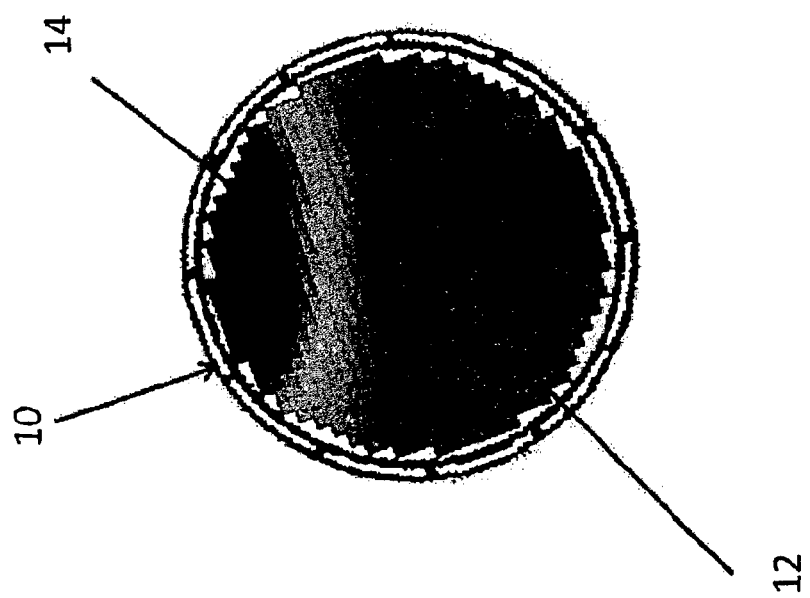

FIG. 17a shows a representation of a mesh of attribute vectors as a cross section of a pipe. In this example the lighter grey color represents liquid oil, 12, present at a mesh point while the darker grey color represents gas, 14. FIG. 17b shows the same attributes but in cross section where the vertical axis represents time. The left hand diagram of FIG. 17b indicates a lower rate of gas flow than the right hand side, the measurements indicating that the gas structures at the lower rate are smaller than those at the higher rate of gas flow.

Figure 18:
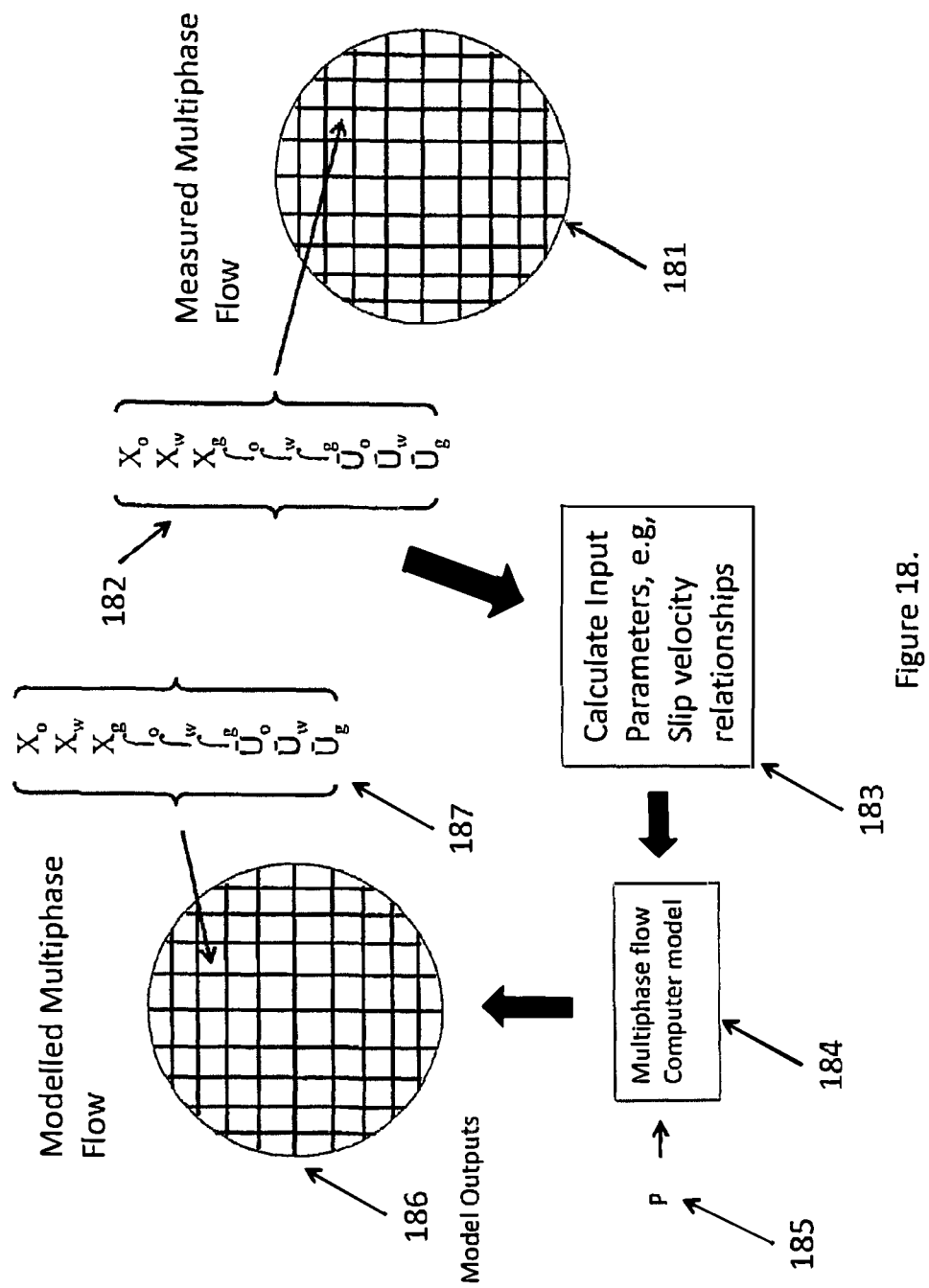
FIG. 18 represents one type of model calibration schema in accordance with an embodiment of the present invention.

The temporal and spatial distribution of the phases can now be used to derive information of value to the management of the oil or gas reservoir producing the multiphase flow. In general, detailed understanding of the phase distributions in a multiphase flow is reliant on sophisticated mechanistic multiphase flow modelling software. The OLGA software package is recognized in the industry as one of the best, see http://www.sptgroup.com/en/Products/OLGA. However, all of these modelling packages depend on input parameters that are often not well known or have been estimated from laboratory experiments and so are extrapolated to representative of the actual field conditions. This has limited their use to planning type applications where 'what if' scenarios are played out in order to better understand the scope of the system design. Even for these planning applications, there are significant uncertainties in their predicted outputs because the models have not been calibrated. Multiphase flow meters in the market today do not provide the spatial distribution of the flow parameters but instead provide single or averaged values across the cross-section of the pipe. Therefore, it has been very difficult to calibrate or validate these sophisticated multiphase models in real field environments. The invention here described provides a new capability to calibrate and validate multiphase flow models enabling them to have wider application in planning and also during real-time production optimization. This has hitherto not been possible. FIG. 18 illustrates one approach disclosed to calibrate a multiphase flow model. In this figure, 181 labels a cross-section of the pipeline, which comprises a mesh or grid of measured flow attributes. Each grid element has a vector of attributes, 182 $D(t)_{I,J}$, which are: $\{X_o, X_w, X_g, \sigma_o, \sigma_w, \sigma_g, \overline{U}_o, \overline{U}_w, \overline{U}_g\}$. These are the measured values of; concentration of oil, water and gas; the density of oil, water and gas; and the velocity of oil, water and gas at each grid location and at a particular point in time. That is, there is a spatial distribution of the parameters that fully characterize the multiphase flow in the pipe. It should be noted that these values are varying with time so that a complete flow description is obtain as a function of time. This information will also be stored for future analysis and in particular to provide historical data with which to calibrate multiphase flow models. In the simplest form of calibration shown in FIG. 18, parameters used by the model that are obtained from, for example, laboratory experiments or correlations, can be computed directly from the measured output parameters. A typical example is what is called the 'slip velocity'. Generally, the different phases flowing in a pipeline will move at different velocities. For example, gas bubbles moving in oil or water can travel at a different velocity to the oil or water in which they are entrained. This velocity difference is often called the gas/oil or gas/water slip velocity. Its value varies depending on several parameters, e.g., the size of the gas bubbles, the inclination of the pipe and on the physical characteristics of the different phases, e.g., density differences. The results generated by the multiphase flow model is very depended on the gas slip velocities and typically, the values are derived from correlations (or look-up tables) obtain during laboratory experiments that are clearly not fully representative of the in situ pipeline conditions. It is provided in this invention that measured values of the different phase velocity distributions will be used as direct input into the multiphase flow model and in particular the $\overline{U}_o$, $\overline{U}_w$ and $\overline{U}_g$ values can be used to directly calculate the gas/oil and gas/water slip velocities. It is also possible to compute other parameters including the in situ density of the different phases. These input parameters are labelled 183 in FIG. 18 and they used as input into the multiphase flow model shown as 184. The parameters, P, 185, are static parameters that represent, for example, the geometry of the pipe or its inclination etc. and they do not change from simulation to simulation at a particular location in the pipe. The calibrated model 184 can then be used to provide a computed or modelled temporal and spatial distribution of the multiphase flow, as labelled 186 in FIG. 18. Each grid element in the modelled output will comprise a computed vector, $M(\theta_t)_{I,J}$: $\{X_o, X_w, X_g, \sigma_o, \sigma_w, \sigma_g, \overline{U}_o, \overline{U}_w, \overline{U}_g\}$. These are the modelled values of; concentration of oil, water and gas; the density of oil, water and gas; and the velocity of oil, water and gas at each grid location at a particular simulated location and at a particular point in time. Clearly the calibrated model, 184, can now be used to produce modelled results anywhere along the pipeline and at any point in time, and so can be used to analyze the multiphase flow conditions. Those skilled in the art will appreciate that other model input parameters in addition to the gas slip velocity, can be derived from the measurement grids 181 for use in the calibration process shown in FIG. 18 and all are provided in this invention.

Figure 19:
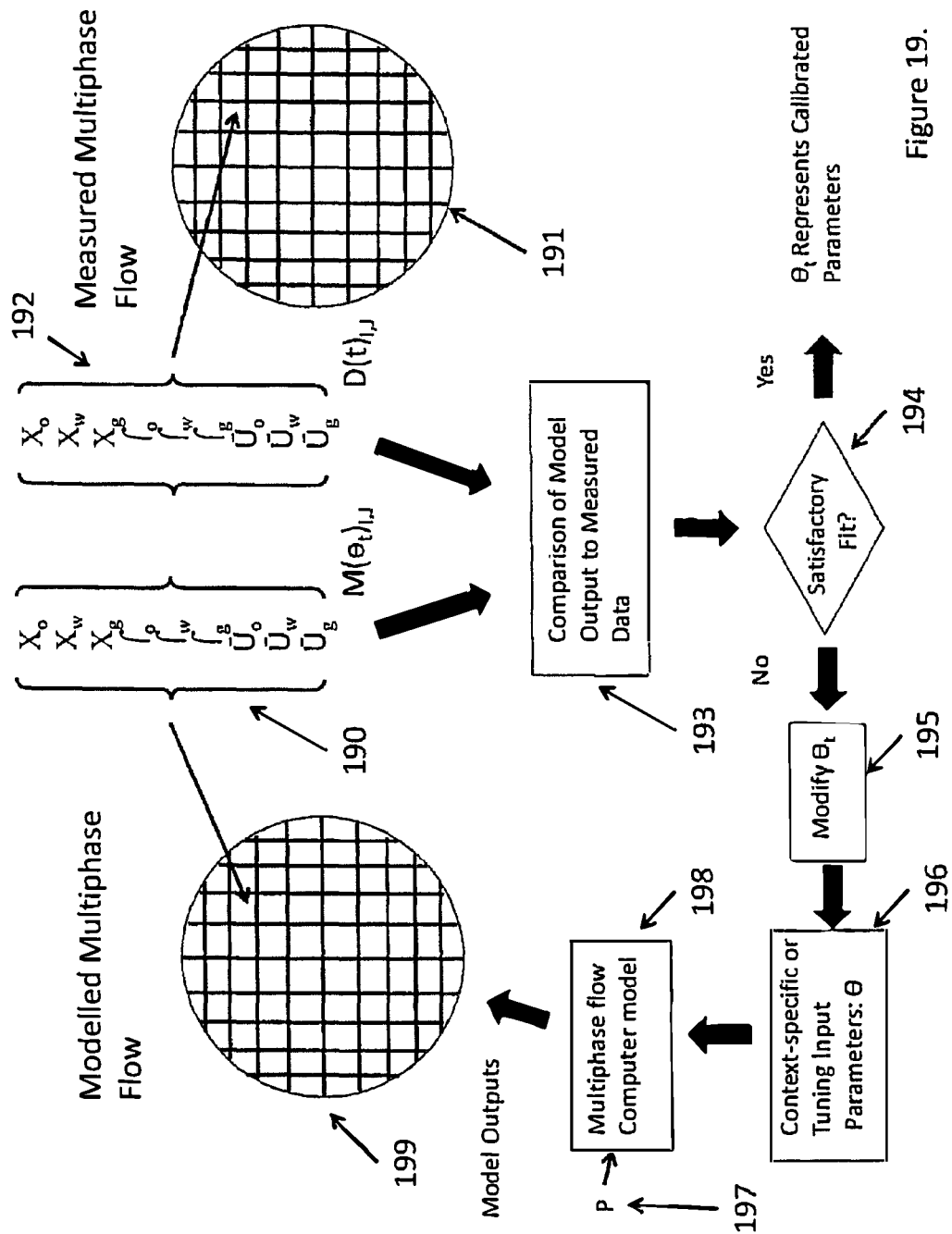
FIG. 19 represents a generalized form of model calibration in accordance with an embodiment of the present invention.

FIG. 18 represents one type of model calibration schema where certain input parameters or relationships are computed directly from the measured data, however, there are many others. FIG. 19 will be used to describe a generalized form of calibration with a preferred embodiment. In general, calibration consists of searching for a set of values of one or more context-specific or tuning inputs such that the observed data fit as closely as possible, in some sense, to the corresponding modelled outputs. A perfect fit is rarely achievable, therefore the adjustment of model input parameters continues until the error between the model output and the corresponding measured data is minimized or reduced to a level that is considered acceptable.

The principle steps are:
1) Build a description of multiphase flow properties using all the available inputs. This includes static information, for example, pipe diameter, pipe inclination etc., and are labeled P, 197, in FIG. 19. The inputs also include context-specific or tuning parameters, θ, in FIG. 19. It should be noted that θ is a vector of parameters that can include, for example, fluid property data, viscosities, densities, mass transfer coefficients between phases as pressure and temperatures change (PVT relationships), slip velocities between phases etc. These parameters may vary both spatially and temporally such that they represent specific flow conditions.
2) Forward modeling of the multiphase flow system to compute a cross section of the pipe made up of pixels or grid points where each pixel has a computed vector; $\{X_o, X_w, X_g, \sigma_o, \sigma_w, \sigma_g, \overline{U}_o, \overline{U}_w, \overline{U}_g\}$, 190, that represents the concentration of oil, water and gas; the density of oil, water and gas; and the velocity of oil, water and gas at each pixel, respectively, and at a particular point in time. This is best done using a mechanistic approach governed by conservation of mass, momentum and energy, coupled with fundamental thermodynamics and heat transfer. Commercial models such as OLGA can be used to carry out this step.
3) Match forward modeled results to measured pipe cross-sections that are made up of pixels containing the same vector $\{X_o, X_w, X_g, \sigma_o, \sigma_w, \sigma_g, U_o, U_w, U_g,\}$, 192, and quantify the cumulative error between the modeled and observed data sets.

4) Determine if the computed error is a minimum or is acceptable and if not;
5) Modify context-specific or tuning parameters and return to step 2.

The above workflow can be carried out using historical or recorded measured data or more preferably can be performed in real-time as new measurements of are obtained. It should be noted that both modelled and measured data sets are vectors varying spatially and with time. In FIG. 19, $D(t)_{I,J}$ represents the measured data set at pixel or grid point I,J, at time, t, and $M(\theta_t)_{I,J}$ represents the modelled output data set at pixel or grid point I,J when using the input parameter vector $\theta$ at time, t. When the error between measured and modelled data is minimized or acceptable, in step 4, the input vector $\theta$ at this point represents the calibrated parameter vector.

FIG. 19 represents a workflow that can be applied to several computational schemas. As an example, a stochastic methodology using Genetic Algorithms can be applied. Examples are provided by C-Y Cheng, X-Y Wu and K. W Chau in a paper titled "Multiple Criteria Rainfall Run-off Model Calibration using a Parallel Genetic Algorithm in a Cluster of Computers", Hydrological Sciences Journal, 2005 and also by P. J. Ballester and J. N Carter in a paper titled "Model Calibration of a Real Petroleum Reservoir using a Parallel Real-coded Genetic Algorithm", IEEE Congress on Evolutionary Computation, 2007. Both papers describe the calibration of multi-variant simulation models using measured data sets as inputs to the process. The principle of operation of a genetic algorithm is that sets of parameter vectors used as inputs to model simulation runs are considered to represent a 'generation'. Those parameter vectors that produce model results that most closely fit the measured data are combined to create 'children' of parameter vectors that contain the attributes of their parents. Those parameter vectors that badly fit the measured data are discarded. The objective being to 'evolve' to the best solution through a process similar to natural selection as occurs in nature. The basic steps are as shown in the flow chart in FIG. 19. The process starts with a population of randomly generated parameter vectors. In reality these input parameter vectors will be constrained so that certain parameters fall within physically viable values, e.g., the viscosity of oil has a range of realistic values and so this input parameter should be chosen to fall within this range. At any iteration of the process, the parameter vector is labelled as 196 in FIG. 19. In a genetic algorithm the model is run with each of the parameter vectors and the information describing a candidate solution is encoded into a data structure (referred as the genome). This is shown in step 198 and the resulting computed model outputs are shown as 199 and 190. The 'fitness' of each solution is determined by use of an objective function that quantifies the misfit between model prediction and the measured data sets, for example, a sum of squares error could be used. This process is illustrated in steps 193 and 194 in FIG. 19. Multiple individuals (that is, input parameter vectors) are selected from the current population depending on their fitness and are modified or combined to create a new set for parameter vectors, that is, the next generation. The combination can be achieved using many differing schemas, for example, the input parameters could be statistically combined, for example, averaged. Those skilled in the art will recognize that many combining (mutation) functions can be used. The resulting next generation population of parameter vectors is then used to run a new series of model results to be compared with the measured data sets and to obtain yet another generation of parameter vectors. This is carried out in the step 195 shown in FIG. 19. The process continues until either a maximum number of generations is reached or a good enough fit between modelled results and measured data is achieved. At this point a resulting input parameter vector $\theta$ represents the calibrated parameters, as illustrated when the result of the Boolean operation labelled 194 is 'Yes'.

A preferred methodology is the use of a Bayesian approached as described by M. C. Kennedy and A. O'Hagan in a paper titled "Bayesian Calibration of Computer Models" Journal of the Royal Statistical Society, 2001; by R. D. Wilkinson in a paper called "Bayesian Calibration of Expensive Multivariate Computer Experiments", published by John Wiley and sons, 2001 in a booked titled "Computational Methods for Large-scale Inverse Problems and Quantification of Uncertainty"; and by Ole Petter Lodoen and Hakon Tjelmeland at the Department of Mathematical Sciences, Norwegian University of Science and Technology, Trondheim, Norway in a paper titled "Bayesian Calibration of Hydrocarbon Reservoir Models Using an Approximate Reservoir Simulator in the Prior Specification". In the later example, a reservoir simulator solving a set of partial differential equations, uses the reservoir properties as context-specific inputs and gives the production properties as outputs. The calibration problem, often called history matching in reservoir modelling, is to infer the reservoir properties from observed production history, that is, measured data. This is achieved by finding the input parameter vector(s) that produce modelled results that most closely represent the measured production data sets. This approach is utilized and formulated so that the mechanistic model, 198, replaces the reservoir simulator and multiphase flow spatial and temporal distributed values are computed as outputs, 199 and 190 in FIG. 19. Measurements of the same spatial and temporal multiphase flow parameters, 191 and 192 in FIG. 19, represent the historical data used to calibrate the model, 198. The input parameter vector $\theta$ that provides the closest fit of the model data to the measured values represent the calibrated input parameter vector.

The Bayesian approach provides several advantages that make it well suited to applications where model computations can be expensive in computer resources to run. This is true of reservoir simulation problems, hydrogeological simulations or weather predictions where models are extremely complex. It is also true where simulations are required very quickly for use in real-time, or within a few seconds, for comparison with real-time measurements. It treats the model as a 'black box' and no use of the information about the mathematical implementation of the model is required. This simplifies the implementation of the process illustrated in FIG. 19. The Bayesian approach also allows for all sources of uncertainty to be considered, this includes, for example, input parameter vector uncertainty, model inadequacy (some processes may include assumptions) and observation errors (variation in measured data sets). In addition, the Bayesian approach allows the capture and use of 'beliefs' about the model from, for example, experts input. As an example, prior knowledge of the distribution or shape of the function that relates inputs to outputs, for example, do we expect linear or quadratic, smoothness and variation of output, for example, what kind of length scale is the function expected to vary over. The implementation involves using a limited ensemble of models runs to train a meta-model of the full simulator, sometimes referred to as an emulator (see, Sacks et al. 1989). The emulator provides a statistical description of the 'beliefs' about the simulator and can be used as a cheap replacement for the simulator in the calibration process. In FIG. 19, 198 represents this faster model when this approach is taken. Principle component analysis is used to project the multivariate model output onto a lower dimension input space and Gaussian processes to emulate the map from the input space to the lower dimension space and to reconstruct from the subspace to the original space. This provides a means of bypassing the expensive multivariate simulation model with a combination of dimension reduction and emulation in order to perform calibration. A full description can be found in the Wilkinson paper referenced above.

While a few embodiments of the multiphase flow model calibration process are provided above, those skilled in the art will appreciate that there are many other computation methods that can be applied in order to realize the process schematically illustrated in FIG. 19 and all are provided in this invention.

A further aspect of this invention is the combination of the spatial and temporal distributions of multiphase flow attributes as measured by an apparatus described in several embodiments of this invention with the calibrated mechanistic multiphase flow model, as described previously in other embodiments of this invention, to control process parameters in order to improve production performance of an oil/gas well or group of oil/gas wells or oilfield. This further aspect will now be described along with embodiments using FIGS. 20 and 21.

Figure 20:
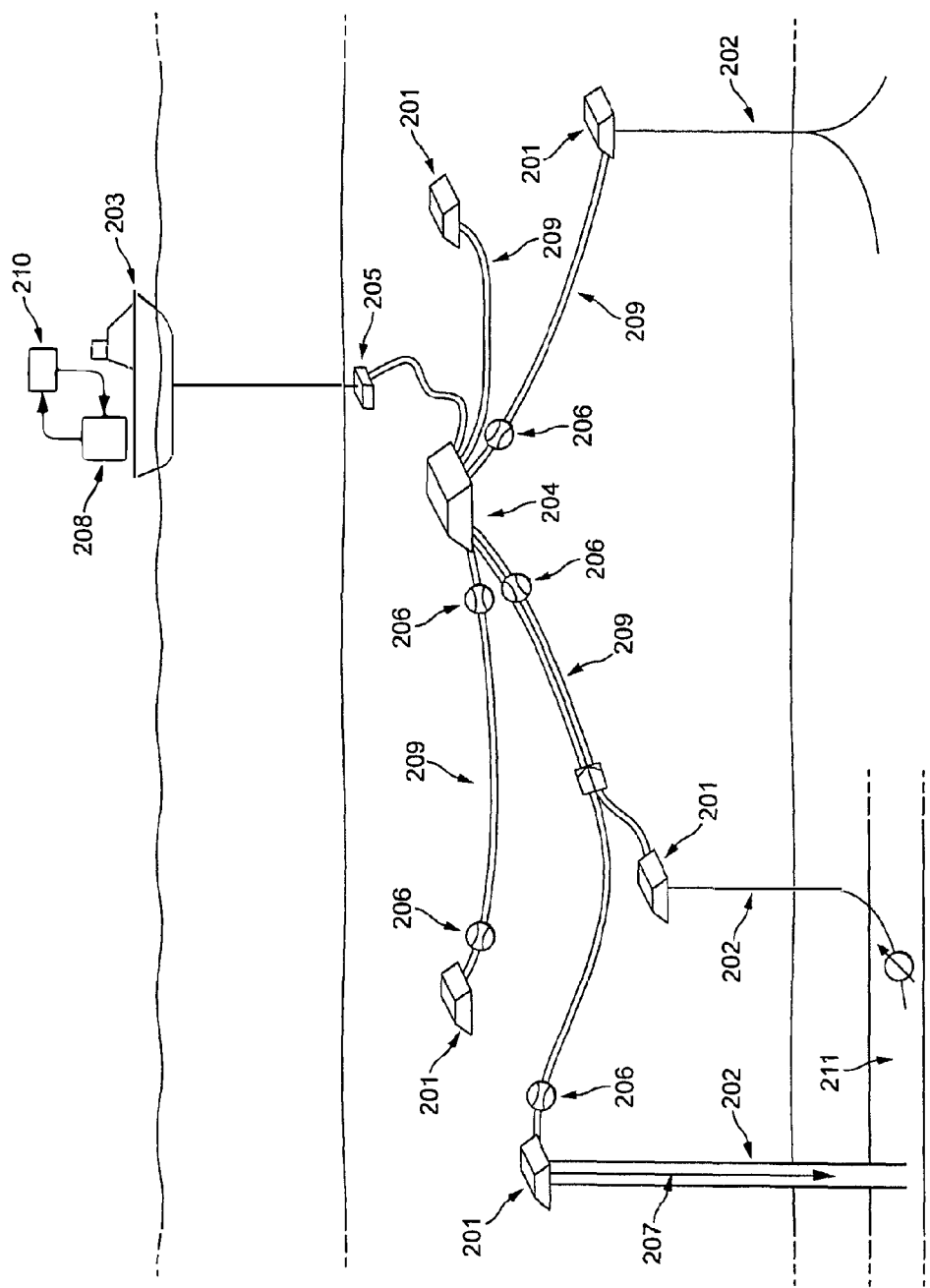
FIG. 20 shows a schematic of the principle components of a subsea oilfield production installation in accordance with an embodiment of the present invention.

FIG. 20 shows a schematic of the principle components of a subsea oilfield production installation. The figure shows a field of 5 wells labelled 201 connected using pipelines or flowlines, 209, (the terms pipeline and flowlines will be used interchangeably in this invention) to a subsea manifold, 204. Production from the wells flow through the pipelines on the seabed labelled 209. It should be noted that the pipelines labelled 209 can comprise a bundle of pipelines used not only to transport production fluids from the wells but also to transport gas from compressor units on surface; electrical and hydraulic control lines from the surface control system, 208, to valves, chokes, pumps etc., that will be used to control overall production from the wells (including downhole, i.e., subsurface); power from surface to subsea and/or downhole equipment and instrumentation; and cables to carry measurement data from instrumentation to the surface control system. The network shown here is relatively simple and in some installations the number of wells can be in the tens or even hundreds. The system can include multiple manifolds, 204, collecting production from many wells. In FIG. 20, the flow is collected at the manifold 204 is co-mingled and transferred to a surface through a single pipeline 205. At surface there is a FPSO (Floating Production Storage and Offloading) unit 203. This could equally be some other form of production platform. On the FPSO there is a system control unit, 208 connected to a calibrated multiphase flow model(s), 210, as described in other embodiments of this invention. In FIG. 20, 5 multiphase flowmeters are shown labelled 206 and as described in other embodiments of this invention. It will be appreciated that there could be more or less of these meters depending on the requirements and complexity of the system. It will also be apparent that some of these multiphase flowmeters could be installed downhole in the wells, that is, subsurface as illustrated by 211. While the schematic shown in FIG. 20 represents a subsea production system, those skilled in the art will appreciate that the embodiment described equally applies to a land based production system.

In the simplest terms the multiphase flow model(s) (note there could be several models where each represents a particular subsystem) is calibrated using data acquired using the multiphase flowmeters, 206, using methods described in other embodiments of this invention. The calibrated model can then be used to provide distributed spatial and temporal multiphase flow attributes at points in the flow system where a measurement does not exist or predictions of multiphase flow behavior at some future time. It should be noted that spatially in this context refers to both on a grid across the cross-section of the pipeline and/or on any cross-section of the pipeline system. Such information is unique and invaluable to the reservoir or production engineers for use to improve oil or gas production. An embodiment will now be described by use of the flow chart shown in FIG. 21.

Figure 21:
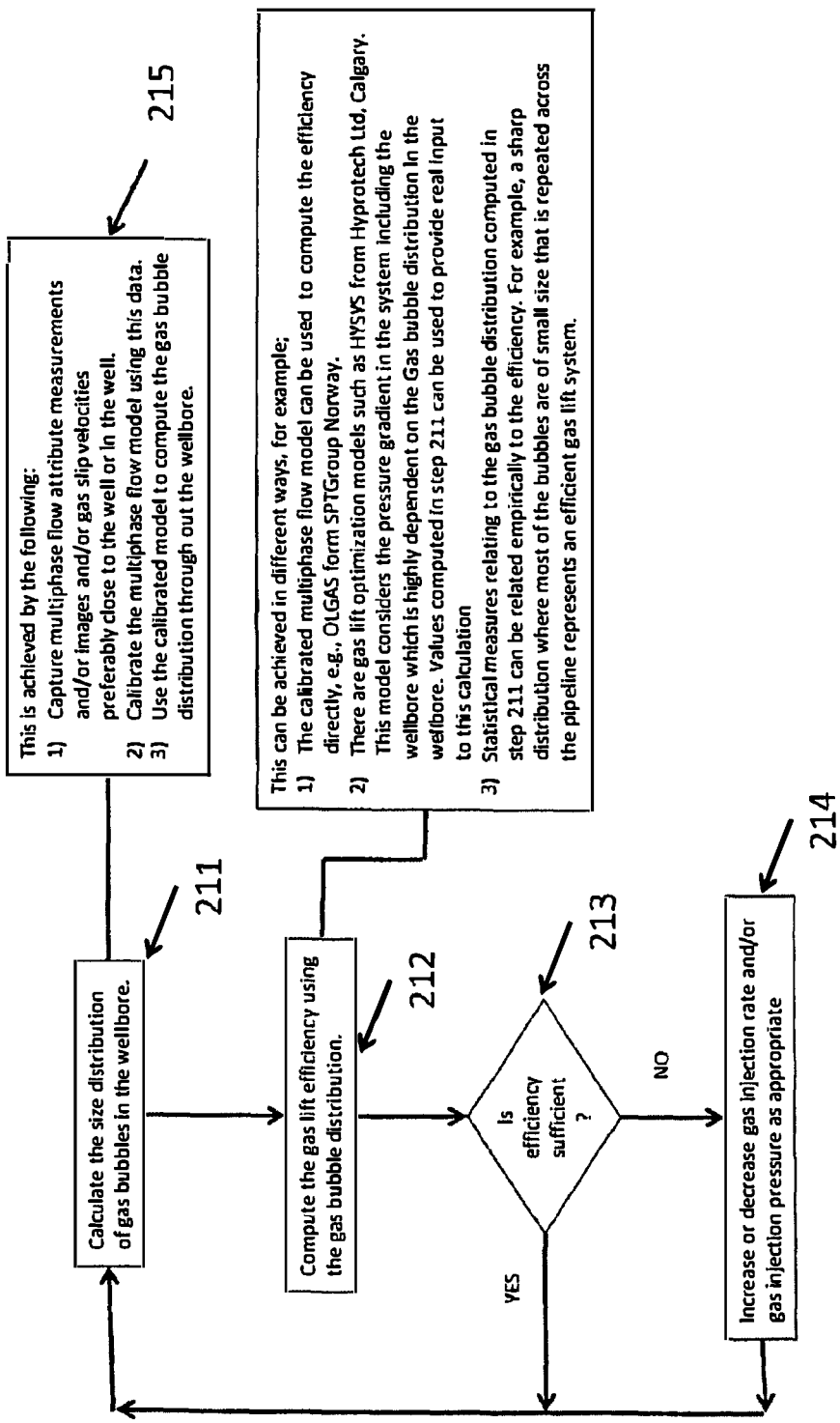
FIG. 21 shows a flow chart of a process for controlling gas lifting efficiency of an oilfield production installation in accordance with an embodiment of the present invention.

The first example aims to improve the operation of gas lifting. As oil or gas is produced from a well, the pressure in the reservoir is reduced. This pressure is responsible for pushing the oil out of the well and to surface. It must be greater than the hydrostatic head of the fluids in the well that creates a pressure in the opposite direction at the bottom of the well. Once depletion has reached the point where the reservoir pressure is no longer greater than this hydrostatic head of fluids in the well, flow from subsurface to surface stops. In order to flow again the well needs secondary recovery procedures where energy is added to the reservoir to increase the pressure or where the hydrostatic head in the well is reduced. That is, the procedure provides an artificial drive to replace the natural drive. Pumps such as beam pumps and electrical submersible pumps are often used. Another secondary drive method is to inject gas into the bottom of an active well, which will displace some the fluid in the well so that the overall density of the fluid in the wellbore is reduced. This in turn reduces the hydrostatic head of the fluid in the well so that it is no long lower than the reservoir pressure and production can continue. The method is known as gas lifting and is commonly used in the oilfield and is well known to those skilled in the art. In FIG. 20 this is illustrated where the gas injection line is shown labelled 207. The line passes down into the well and gas is injected through it (and through gas lift valves) using compressors (or reservoirs) to supply air or Carbon dioxide or Nitrogen or some other gas, not shown in FIG. 20. The flowrate and pressure of the injected gas is controlled by the surface control unit, 208 so that these gas injection parameters can be increased or decreased as required. The performance of the secondary production is highly dependent on these injection parameters and they will be influence by specific well, reservoir and fluid conditions. An ideally scenario is that the injected gas is evenly distributed as small gas bubbles in the production stream. In this case, the wellbore fluid density is uniformly reduced and gas lifting is very efficient resulting in improved production. In addition, the transition from a bubble flow regime (efficient gas lifting) to a slug flow regime (low efficiency gas lifting) requires larger concentrations of gas when the bubble size is small. As an example, experiments show that the transition changes from 10% gas fraction when average bubbles size is ~13 mm to 30% when the bubble size is ~7 mm, that is, significantly more gas can be injected for gas lifting before slugging occurs when the bubble size is small (see, "Bubble Size Effect on Gas Lifting", Sebastien Guet, Delft University Press, 2004). If, on the other hand, the gas travels as unevenly distributed large bubbles the density is not uniform causing slugging and in a worst case scenario, a gas channel occurs where gas flows very rapidly to surface, "short-circuiting" the production flow, this is condition is often referred to as annular gas flow. In this case, gas lifting is at a very low efficiency. In addition, larger bubbles generally travel with larger velocities than small ones. As a result the gas residence time in the wellbore is much reduced when the flow consists of mostly larger bubbles and the gas lift efficiency is reduced. Therefore, the production engineer needs to adjust the gas rate and or pressure so that an even distribution of small gas bubbles is generated. It should also be noted that this is a dynamic process that needs to be adjusted continually as, for example, the production flow rate changes. However, previously this was very difficult and relied on a 'trial and error' approach because the production engineer had no way of knowing the actual distribution of gas in the wellbore. The multiphase flowmeter described in this invention provides a solution to this problem and parameters such as cross-sectional gas fraction, average bubble size, average gas slip velocity and their distribution over the pipe cross-section can be measured. FIG. 21 shows a flowchart that captures an embodiment of this invention.

Referring to FIG. 21, the first step, 211, is to calculate a parameter (or set parameters) that quantifies the gas bubbles size distribution within the wellbore. It is very unlikely that there will exist multiple multiphase flowmeters within the wellbore to provide a direct measurement of this distribution; however, a multiphase flowmeter in the pipeline on the seabed close to the wellhead and/or somewhere along the pipeline is proposed in this embodiment. This multiphase flowmeter provides measurements of the distribution of attributes of the different phases across the pipeline as described in other embodiments of this invention. For example, the multiphase flowmeter will provide images or a grid of the gas bubble distribution across the pipeline or the different phases slip velocities. These measurements are available continuously in time. The grids of measured multiphase flow attributes are used to calibrate a multiphase flow model as described in other embodiments. The calibrated model can then be used to accurately compute the gas bubble distribution anywhere within the pipeline system and more particularly throughout the wellbore. The next step is to use the gas bubble distribution to evaluate the efficiency of the gas lifting operation. This can be achieved in different ways that will now be described but those skilled in the art will appreciate that there can be other methods to use this information to achieve the same result. These other methods are provided in this invention.

In step 212 the objective is to evaluate the efficiency of the gas lift operation using the wellbore gas bubble distribution obtained in step 211. Some examples of how to achieve this are given below, however, those skilled in the art will appreciate that other methods using the distribution measurements could be used:

1) Some commercially available multiphase flow models provide a gas lift sub-model or "plug-in" to directly evaluation the efficiency of gas lifting. Generally these are used in the planning phases for design of the system. However, by calibration of the model as described in step 211 above, it is now possible to use these tools in real-time to provide continuous gas lift efficiency values. An example, commercial model is OLGAS from the SPT Group in Norway.
2) Commercially there are gas lift modeling software tools specifically designed for optimization. An example is HYSYS from Hyprotech Ltd., in Canada. This model uses the pressure gradient in the system including in the wellbore, which is highly dependent on the gas bubble distribution in the wellbore. The distribution values computed in step 211 can be used to provide a real input to this calculation.
3) Statistical measures obtained from the wellbore gas bubble distribution can be empirically related to the efficiency of the gas lift operation. For example, a bubble size distribution where most of the bubbles are small in size, and where this is repeated across the cross-section of the wellbore, represents an efficient gas lift system. Those skilled in the art will appreciate that statistics that are computed from measurements of gas bubble sizes and quantities can be used. Measures such as mean, standard deviation, skew or kurtosis can be employed to quantify bubble size distribution. Image processing techniques (see, for example, an article titled "Creating a system to analysis air bubbles in liquids using LabView" by Ernest Wilding published on the National Instruments website, www.nl.com) can also be applied to multiphase flow parameter grids of gas concentration, to obtain bubble distribution information cross the cross-section of the pipeline. For example, an image of an even distribution of small bubbles across the cross-section of the pipeline is a measure of a uniform distribution, whereas a distribution that consists of a small number of large bubbles is an indication of an uneven distribution.
4) Another measured grid value that can be used is the gas slip velocity computed from measured values of the different phase velocity distributions; $\overline{U}_o$, $\overline{U}_w$ and $\overline{U}_g$. It should be noted that these slip velocities are computed at each pixel or grid element across the pipeline and therefore provides a slip velocity distribution over the cross-section. Large gas bubbles will travel up the wellbore much more rapidly than smaller bubbles, which have a tendency to travel at velocities closer to the oil or water velocity in which they are entrained. Therefore, the gas slip velocities within the wellbore can be used to quantify gas bubble size distribution in the wellbore.
5) Yet another method is to use the flow distribution parameter $C_0$ as described by Sebastien Guet, "Bubble Size Effect on Gas Lifting", Delft University Press, 2004. This parameter quantifies the transfer profile of void fraction and phase velocities, thus depends on the radial gas fraction profile and captures the bubble size dependency. A value of $C_0<1.0$ results in best gas lift efficiencies, values $1.0<C_0<1.1$ provide intermediate efficiencies and $C_0>=1.2$ represents slug flow and are to be avoided. The value of $C_0$ can be computed from distributed measurements described in other embodiments of this invention as follows:

$$C_0=(R^2/2)(\int \varepsilon j r dr/(\int \varepsilon r dr \int j r dr))$$

Where $\varepsilon$ is the local void fraction, $j=\varepsilon\overline{U}+(1-\varepsilon)U_l$ is the local mixture volumetric flux and R is the pipe radius. $\varepsilon$ is the local void fraction obtained directly from the concentration measurements ($X_o$, $X_w$, $X_g$) and $U_l$ is obtained from the velocity of oil or water ($\overline{U}_o$, $\overline{U}_w$) depending on which is the continuous phase in the flow determined from the concentrations. It should be noted that it is assumed in the equation above that there is radial symmetry but this is not necessary as the measurements as described in other embodiments of this invention are made independently over the cross-section of the pipe and so the integration can take place over the area.

After the gas lift efficiency has been quantified in 212, it will be evaluated to establish if it is sufficient/appropriate or optimal for the current operation. This can be as simple as determining if it is greater than a predefined threshold provided by the production engineer. It could also be determined interactively by intervention from the production engineer. The method is not critical but preferably it is achieved programmatically so that the workflow shown in FIG. 21 is automated.

If it is determined that the efficiency is sufficient then the process returns to step 211 and is repeated. However, if it is determined that the gas lifting is inefficient, then the workflow continues to step 214 where the gas lift process parameters of gas injection pressure and/or flowrate are modified. The determination of the new control parameters can be obtained by use of commercial gas lifting modelling software such as HYSYS or preferably by forward modelling of the calibrated multiphase flow model, 210. In this case the model is run using different gas injection rate parameters until it predicts an optimized gas lifting and thus a desired wellbore gas bubble distribution. This process is linked to the embodiment previous described in FIG. 19. The model provides the resulting gas injection parameters to the surface control system, 208 and the workflow returns to step 211 and is repeated. It should be noted that the step 214 could be performed interactively by manual intervention of the production engineer. In this case, he/she will run the calibrated multiphase flow model or the gas lift optimization model to obtain the new gas injection parameters and input these parameters manually into the surface control system, 208. Preferably the process described in FIG. 21 is performed automatically; however, both automated and manual control of the process are provided in this invention.

Those skilled in the art will appreciate that the gas lift example provided is just one of many operations that can be improved or optimized in a similar fashion. For example, the determination of production gas slugging in the subsea pipelines is very important from a safety point of view as well as from a production optimization point of view. When large slugs of produced gas reach the FPSO undetected they pose a major safety concern. If, on the other hand, their development is detected then the well from which the gas originated can be choked to control the rate at which the gas is produced. By providing multiphase flowmeters, 206 that provide cross-sectional measurements of the phase distributions in the pipeline, gas slugs can be readily identified early. In addition, by using such measurements to calibrate a multiphase flow model, as described above, the model can be used to more accurately predict the development of slugging at locations where a measurement is not available and, again, can readily be used to identify production gas slugging. Another example is the control of Electrical Submersible Pumps (or other downhole pumps) to improve or optimize production. The workflow is similar to that shown in FIG. 21 where the pump control parameters are obtained in place of the gas injection parameters shown in FIG. 21. Yet other examples include the management of the injection of inhibitor chemicals that need to be placed where hydrate or wax build up are possible. A calibrated multiphase flow model will more accurately determine where these problems can occur in the pipeline system and how much chemicals and where they are required to prevent the build up of hydrate or wax.

The surface control system 208 will be used to control valves and chokes that exist in the wells or on the seabed where the produced multiphase flow enters the subsea flowlines 209. The use of multiphase flowmeters providing phase distribution flow characteristics across the pipeline and in conjunction with a calibrated multiphase flow model as described previously, allows the production engineer to identify production issues early and so take corrective action. As an example, if the amount of water produced from a well is increasing, the production engineer can use the control system 208 to choke back the flow from the reservoir zone that is producing the water.

Those skilled in the art will appreciate that a wide range of production processes can be controlled significantly more effectively with the use of multiphase flowmeters that provide cross-sectional images and phase parameter distributions in the pipeline. They will also appreciate that this is especially true when multiphase flow models are calibrated using such multiphase flowmeters and thus can be used to provide accurate predictions anywhere in the production flow system at any point in time. In particularly, such predictions can be used to determine the system control input parameters that result in improved or optimized production. As a result, Multiphase flowmeters as described provide a means to calibrate and validate numerical production models from within the reservoir all the way though the well facility and pipelines to the export point, that is capable of self learning. The control of all such production processes utilizing such multiphase flowmeters and/or such calibrated multiphase flow models is provided in this invention.

What is claimed is:

1. A method of defining a multiphase flow comprising three phases, the method comprising: simultaneously measuring electromagnetically, directly or indirectly, at a plurality of positions across a cross-section of the flow, (a) the individual concentration of each of the three phases; (b) the individual density of each of the three phases; and (c) the individual velocity of each of the three phases; wherein the measured concentration, density and velocity values of the three phases constitute nine parameters representing the multiphase flow, and processing the measured concentration, density and velocity values of the three phases into a form representing the respective concentration, density and velocity of the phases across plural cells of a cellular grid extending across at least a portion of a cross-sectional area of the flow.

2. A method according to claim 1 wherein the three phases comprise a gas phase, and oil phase and an aqueous phase.

3. A method according to claim 2 wherein the gas is natural gas and the oil is mineral oil, and the three phases are output from an oil well.

4. A method according to claim 1 further comprising comparing an image, or mathematical representation of an image, related to the measured concentration, density and velocity values of the three phases to a stored or modelled image, or mathematical representation of a stored or modelled image of the concentration, density and velocity values of the three phases.

5. A method according to claim 1 further comprising controlling the multiphase flow in response to the measured concentration, density and velocity values of the three phases.

* * * * *